(12) United States Patent
Takahashi et al.

(10) Patent No.: US 9,156,838 B2
(45) Date of Patent: Oct. 13, 2015

(54) FUSED HETEROCYCLIC COMPOUND

(71) Applicant: Sumitomo Chemical Company, Limited, Tokyo (JP)

(72) Inventors: Masaki Takahashi, Takarazuka (JP); Takamasa Tanabe, Takarazuka (JP); Mai Ito, Takarazuka (JP); Chie Shimizu, Takarazuka (JP); Yoshihiko Nokura, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/408,598

(22) PCT Filed: Jun. 12, 2013

(86) PCT No.: PCT/JP2013/066767
§ 371 (c)(1),
(2) Date: Dec. 17, 2014

(87) PCT Pub. No.: WO2013/191188
PCT Pub. Date: Dec. 27, 2013

(65) Prior Publication Data
US 2015/0246911 A1    Sep. 3, 2015

(30) Foreign Application Priority Data
Jun. 22, 2012 (JP) ................. 2012-140586

(51) Int. Cl.
| C07D 498/04 | (2006.01) |
| C07D 471/04 | (2006.01) |
| A01N 43/90 | (2006.01) |
| C07D 263/57 | (2006.01) |
| A01N 43/76 | (2006.01) |

(52) U.S. Cl.
CPC .............. C07D 471/04 (2013.01); A01N 43/76 (2013.01); A01N 43/90 (2013.01); C07D 263/57 (2013.01); C07D 498/04 (2013.01)

(58) Field of Classification Search
CPC .................. C07D 471/04; C07D 498/04
USPC .......... 546/113, 114, 115; 514/300, 301, 302
See application file for complete search history.

(56) References Cited

U.S. PATENT DOCUMENTS
| 4,038,396 | A | 7/1977 | Shen et al. |
| 5,104,960 | A * | 4/1992 | Inbasekaran et al. ......... 528/125 |
| 2004/0198768 | A1 | 10/2004 | Park Choo et al. |
| 2004/0209776 | A1 | 10/2004 | Farooq et al. |
| 2014/0018373 | A1 | 1/2014 | Takyo et al. |
| 2014/0194290 | A1 | 7/2014 | Takahashi et al. |

FOREIGN PATENT DOCUMENTS
| EP | 0262845 A1 | 4/1988 |
| GB | 1175013 A | 12/1969 |
| GB | 1445824 A | 8/1976 |
| JP | 2008-308448 A | 12/2008 |
| WO | 8802367 A1 | 4/1988 |

OTHER PUBLICATIONS

Int'l Search Report issued Aug. 20, 2013 in Int'l Application No. PCT/JP2013/066767.

Sluka et al, "2-Phenylbenzimidazoles as Potential Anthelminthics," Collection of Czechoslovak Chemical Communications, Institute of Organic Chemistry & Biochemistry, Prague, Czech Republic, vol. 41, pp. 3628-3634 (Jan. 1976).

Coates et al, "Cyclic Nucleotide Phosphodiesterase Inhibition by Imidazopyridines: Analogues of Sulmazole and Isomalzole as Inhibitors of the CGMP Specific Phosphodiesterase," Journal of Medicinal Chemistry, vol. 36, No. 10, pp. 1387-1392 (May 1993).

* cited by examiner

*Primary Examiner* — Niloofar Rahmani
(74) *Attorney, Agent, or Firm* — Panitch Schwarze Belisario & Nadel LLP

(57) ABSTRACT

This fused heterocyclic compound represented in formula (1) has excellent effectiveness in pest control.

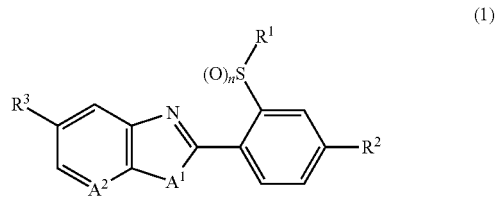

(1)

In the formula, $A^1$ represents $-NR^4-$, etc.; $A^2$ represents a nitrogen atom, etc.; $R^1$ represents an ethyl group, a cyclopropyl group, or a cyclopropylmethyl group; $R^2$ represents $-S(O)_m R^6$ or $-C(R^7)(CF_3)_2$; $R^4$ represents a C1-C6 alkyl group optionally having one or more halogen atoms; $R^6$ represents a C1-C6 haloalkyl group; $R^7$ represents a fluorine atom or a chlorine atom, and m and n each represents 0, 1 or 2.

9 Claims, No Drawings

FUSED HETEROCYCLIC COMPOUND

CROSS-REFERENCE TO RELATED APPLICATION

This application is a Section 371 of International Application No. PCT/JP2013/066767, filed Jun. 12, 2013, which was published in the Japanese language on Dec. 27, 2013, under International Publication No. WO 2013/191188 A1, and the disclosure of which is incorporated herein by reference.

TECHNICAL FIELD

The present invention relates to a fused heterocyclic compound and a use thereof for pest control.

BACKGROUND ART

It is described in WO88/02367 that a fused heterocyclic compound can be used in a medicine.

SUMMARY OF THE INVENTION

The present invention provides a compound having an excellent control effect on pests and a method for controlling pests using the compound.

The present invention is that a fused heterocyclic compound represented by the following formula (1) has an excellent control effect on pests.

More specifically, the present invention is as described below.

[1] A fused heterocyclic compound represented by formula (1) (hereinafter, referred to as the compound of the present invention):

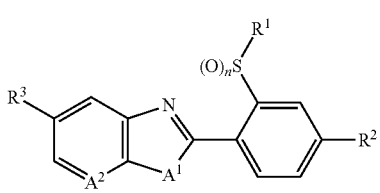

wherein
$A^1$ represents —$NR^4$—, a sulfur atom or an oxygen atom,
$A^2$ represents a nitrogen atom or =CH—,
$R^1$ represents an ethyl group, a cyclopropyl group or a cyclopropylmethyl group,
$R^2$ represents —$S(O)_m R^6$ or —$C(R^7)(CF_3)_2$,
$R^3$ represents a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group,
$R^4$ represents a C1 to C6 alkyl group optionally having one or more halogen atoms,
$R^6$ represents a C1 to C6 haloalkyl group,
$R^7$ represents a fluorine atom or a chlorine atom,
m represents 0, 1, or 2, and
n represents 0, 1, or 2,
wherein when $R^3$ represents a trifluoromethyl group, A represents a sulfur atom and $A^2$ represents a nitrogen atom, and when $A^1$ represents a sulfur atom and $A^2$ represents =CH—, $R^3$ represents a C2 to C3 perfluoroalkyl group, a C2 to C3 perfluoroalkoxy group, a C2 to C3 perfluoroalkylsulfanyl group, a C2 to C3 perfluoroalkylsulfinyl group or a C2 to C3 perfluoroalkylsulfonyl group.
[2]
The compound according to [1], wherein $A^1$ is —$NR^4$—.

[3]
The compound according to [1], wherein $A^1$ is a sulfur atom.
[4]
The compound according to [1], wherein $A^1$ is an oxygen atom.
[5]
The compound according to [1] to [4], wherein $A^2$ is =CH—.
[6]
The compound according to [1] to [4], wherein $A^2$ is a nitrogen atom.
[7]
A pest control composition comprising the compound as defined in any of [1] to [6], and an inert carrier.
[8]
A method for controlling pests comprising applying an effective amount of the compound as defined in any of [1] to [6] to a pest or a pest-infested area.
[9] A compound represented by formula (2):

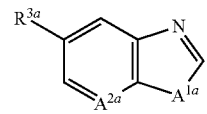

wherein
$A^{1a}$ represents —$NR^{4a}$—, a sulfur atom or an oxygen atom,
$A^{2a}$ represents a nitrogen atom or =CH—,
$R^{3a}$ represents a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, and
$R^{4a}$ represents a C1 to C6 alkyl group optionally having one or more halogen atoms, wherein when $R^{3a}$ represents a trifluoromethyl group, $A^{1a}$ represents a sulfur atom, and $A^{2a}$ represents a nitrogen atom, and when $A^{1a}$ represents a sulfur atom and $A^{2a}$ represents =CH—, $R^{3a}$ represents a C2 to C3 perfluoroalkyl group, a C2 to C3 perfluoroalkoxy group, a C2 to C3 perfluoroalkylsulfanyl group, a C2 to C3 perfluoroalkylsulfinyl group or a C2 to C3 perfluoroalkylsulfonyl group.
[10] A method for producing a compound represented by formula (1):

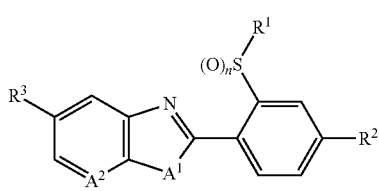

wherein $A^1$, $A^2$, $R^1$, $R^2$, $R^3$, $R^4$, $R^6$, $R^7$, m and n represent the same meaning as described below,
by reacting an intermediate compound (M7):

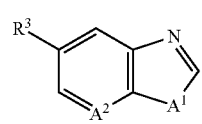

wherein
A¹ is —NR⁴—, a sulfur atom or an oxygen atom,
A² represents a nitrogen atom or =CH—,
R³ represents a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group,
R⁴ represents a C1 to C6 alkyl group optionally having one or more halogen atoms, and
n represents 0, 1, or 2,
with an intermediate compound (M8):

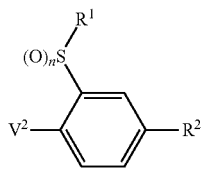

(M8)

wherein
R¹ represents an ethyl group, a cyclopropyl group or a cyclopropylmethyl group,
R² represents —S(O)$_m$R⁶ or —C(R⁷)(CF₃)₂,
R⁶ represents a C1 to C6 haloalkyl group,
R⁶ represents a fluorine atom or a chlorine atom,
V² represents a bromine atom or an iodine atom, and
n represents 0, 1, or 2,
in the presence of a palladium catalyst, a copper catalyst, a ligand and a base.

MODE FOR CARRYING OUT THE INVENTION

The groups used in the description of the present specification will be described below with examples. The notation of Ca to Cb haloalkyl in the present specification represents a straight-chain or branched-chain alkyl group having the number of carbon atoms of a to b, in which one or more hydrogen atoms bound to the carbon atom are substituted by a halogen atom, and at that time, when having two or more halogen atoms, those halogen atoms may be the same or different from each other.

The notation of Ca to Cb perfluoroalkyl in the present specification represents a straight or branched alkyl group having the number of carbon atoms of a to b, in which all hydrogen atoms bound to the carbon atom are substituted by a fluorine atom.

The notation of Ca to Cb perfluoroalkoxy in the present specification represents a straight-chain or branched-chain alkyl —O— group having the number of carbon atoms of a to b, in which all hydrogen atoms bound to the carbon atom are substituted by a fluorine atom.

The notation of Ca to Cb perfluoroalkylsulfanyl in the present specification represents a straight-chain or branched-chain alkyl —S— group having the number of carbon atoms of a to b, in which all hydrogen atoms bound to the carbon atom are substituted by a fluorine atom.

The notation of Ca to Cb perfluoroalkylsulfinyl in the present specification represents a straight-chain or branched-chain alkyl —S(O)— group having the number of carbon atoms of a to b, in which all hydrogen atoms bound to the carbon atom are substituted by a fluorine atom.

The notation of Ca to Cb perfluoroalkylsulfonyl in the present specification represents a straight-chain or branched-chain alkyl —S(O)₂— group having the number of carbon atoms of a to b, in which all hydrogen atoms bound to the carbon atom are substituted by a fluorine atom.

In the notation of "optionally having one or more halogen atoms" in the present specification, when having two or more halogen atoms, those halogen atoms may be the same or different from each other.

The "halogen atom" in the compound of the present invention refers to a fluorine atom, a chlorine atom, a bromine atom, and an iodine atom.

Examples of the "C1 to C6 alkyl groups optionally having one or more halogen atoms" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2,2,2-trifluoroethyl group, and a pentafluoroethyl group.

Examples of the "C2 to C6 alkenyl group optionally having one or more halogen atoms" in the compound of the present invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C1 to C6 haloalkyl group" in the compound of the present invention include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C1 to C3 perfluoroalkyl group" in the compound of the present invention include a trifluoromethyl group, a pentafluoroethyl group, a heptafluoropropyl group, and a heptafluoroisopropyl group.

Examples of the "C1 to C3 perfluoroalkoxy group" in the compound of the present invention include a trifluoromethoxy group, a pentafluoroethoxy group, a heptafluoropropoxy group, and a heptafluoroisopropoxy group.

Examples of the "C1 to C3 perfluoroalkylsulfanyl group" in the compound of the present invention include a trifluoromethylsulfanyl group, a pentafluoroethylsulfanyl group, a heptafluoropropylsulfanyl group, and a heptafluoroisopropylsulfanyl group.

Examples of the "C1 to C3 perfluoroalkylsulfinyl group" in the compound of the present invention include a trifluoromethylsulfinyl group, a pentafluoroethylsulfinyl group, a heptafluoropropylsulfinyl group, and a heptafluoroisopropylsulfinyl group.

Examples of the "C1 to C3 perfluoroalkylsulfonyl group" in the compound of the present invention include a trifluoromethylsulfonyl group, a pentafluoroethylsulfonyl group, a heptafluoropropylsulfonyl group, and a heptafluoroisopropylsulfonyl group.

Examples of the compound of the present invention include the following compounds.
Compounds Represented by Formula (1-1):

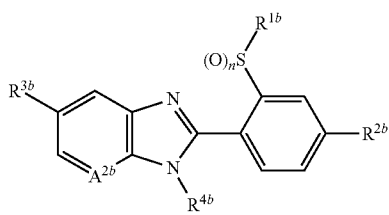

(1-1)

wherein
A²$^b$ is a nitrogen atom or =CH—,
R¹$^b$ represents an ethyl group, a cyclopropyl group or a cyclopropylmethyl group,
R²$^b$ represents —S(O)$_m$CF₃ or —CF(CF₃)₂, $R^{3b}$ represents a C2 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, $R^{4b}$ represents a methyl group or a hydrogen atom, m represents 0, 1, or 2, and n represents 0, 1, or 2.

Compounds Represented by Formula (1-2):

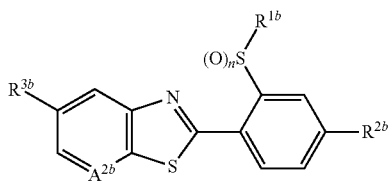

(1-2)

wherein $A^{2b}$ is a nitrogen atom or =CH—, $R^{1b}$ represents an ethyl group, a cyclopropyl group or a cyclopropylmethyl group, $R^{2b}$ represents —S(O)$_m$CF$_3$ or —CF(CF$_3$)$_2$, $R^{3b}$ represents a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, m represents 0, 1, or 2, and n represents 0, 1, or 2, wherein when $A^{2b}$ represents =CH—, $R^{3b}$ represents a C2 to C3 perfluoroalkyl group, a C2 to C3 perfluoroalkoxy group, a C2 to C3 perfluoroalkylsulfanyl group, a C2 to C3 perfluoroalkylsulfinyl group or a C2 to C3 perfluoroalkylsulfonyl group.

Compounds Represented by Formula (1-3):

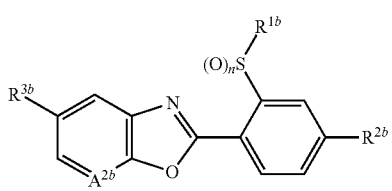

(1-3)

wherein $A^{2b}$ is a nitrogen atom or =CH—, $R^{1b}$ represents an ethyl group, a cyclopropyl group or a cyclopropylmethyl group, $R^{2b}$ represents —S(O)$_m$CF$_3$ or —CF(CF$_3$)$_2$, $R^{3b}$ represents a C2 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, m represents 0, 1, or 2, and n represents 0, 1, or 2.

Formula (1)

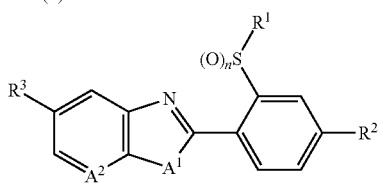

(1)

In the formula (1), compounds wherein $A^1$ is —NR$^4$—;
In the formula (1), compounds wherein $A^1$ is a sulfur atom;
In the formula (1), compounds wherein $A^1$ is an oxygen atom;
In the formula (1), compounds wherein $A^1$ is —NR$^4$—, a sulfur atom or an oxygen atom, and $R^4$ is a C1 to C6 alkyl group optionally having one or more halogen atoms;
In the formula (1), compounds wherein $A^1$ is —NR$^4$—, a sulfur atom or an oxygen atom, and $R^4$ is a C1 to C6 alkyl group;
In the formula (1), compounds wherein $A^1$ is —NR$^4$—, a sulfur atom or an oxygen atom, and $R^4$ is a methyl group, an ethyl group, a propyl group or an isopropyl group;
In the formula (1), compounds wherein $A^1$ is —NR$^4$—, a sulfur atom or an oxygen atom, and $R^4$ is a methyl group;
In the formula (1), compounds wherein $A^1$ is —NR$^4$—, and $R^4$ is a C1 to C6 alkyl group optionally having one or more halogen atoms;
In the formula (1), compounds wherein $A^1$ is —NR$^4$—, and $R^4$ is a C1 to C6 alkyl group;
In the formula (1), compounds wherein $A^1$ is —NR$^4$—, and $R^4$ is a methyl group, an ethyl group, a propyl group or an isopropyl group;
In the formula (1), compounds wherein $A^1$ is —NR$^4$—, and $R^4$ is a methyl group;
In the formula (1), compounds wherein $A^2$ is a nitrogen atom;
In the formula (1), compounds wherein $A^2$ is =CH—;
In the formula (1), compounds wherein $A^2$ is a nitrogen atom or =CH—;
In the formula (1), compounds wherein $A^1$ is —NR$^4$—, and $A^2$ is a nitrogen atom;
In the formula (1), compounds wherein $A^1$ is —NR$^4$—, and $A^2$ is =CH—;
In the formula (1), compounds wherein $A^1$ is —NR$^4$—, $R^4$ is a methyl group, and $A^2$ is a nitrogen atom;
In the formula (1), compounds wherein $A^1$ is —NR$^4$—, $R^4$ is a methyl group, and $A^2$ is =CH—;
In the formula (1), compounds wherein $A^1$ is a sulfur atom, and $A^2$ is a nitrogen atom;
In the formula (1), compounds wherein $A^1$ is a sulfur atom, and $A^2$ is =CH—;
In the formula (1), compounds wherein $A^1$ is an oxygen atom, and $A^2$ is a nitrogen atom;
In the formula (1), compounds wherein $A^1$ is an oxygen atom, and $A^2$ is =CH—;
In the formula (1), compounds wherein $R^1$ is an ethyl group, a cyclopropyl group, or a cyclopropylmethyl group;
In the formula (1), compounds wherein $R^1$ is an ethyl group;
In the formula (1), compounds wherein $R^1$ is a cyclopropyl group;
In the formula (1), compounds wherein $R^1$ is a cyclopropylmethyl group;
In the formula (1), compounds wherein $R^2$ is a C1 to C6 haloalkylsulfanyl group, a C1 to C6 haloalkylsulfinyl group, or a C1 to C6 haloalkylsulfonyl group;
In the formula (1), compounds wherein $R^2$ is a C1 to C3 perfluoroalkylsulfanyl group, a C1 to C3 perfluoroalkylsulfinyl group, or a C1 to C3 perfluoroalkylsulfonyl group;
In the formula (1), compounds wherein $R^2$ is a trifluoromethylsulfanyl group, a trifluoromethylsulfinyl group, or a trifluoromethylsulfonyl group;
In the formula (1), compounds wherein $R^2$ is a heptafluoroisopropyl group;
In the formula (1), compounds wherein $R^2$ is a trifluoromethylsulfanyl group, a trifluoromethylsulfinyl group, a trifluoromethylsulfonyl group, or a heptafluoroisopropyl group;
In the formula (1), compounds wherein $R^1$ is an ethyl group, a cyclopropyl group or a cyclopropylmethyl group, and $R^2$ is a trifluoromethylsulfanyl group, a trifluoromethylsulfinyl group, a trifluoromethylsulfonyl group or a heptafluoroisopropyl group;
In the formula (1), compounds wherein $R^3$ is a C1 to C3 perfluoroalkyl group, a C1 to C3 perfluoroalkoxy group, a C1 to C3 perfluoroalkylsulfanyl group, a C1 to C3 perfluoroalkylsulfinyl group, or a C1 to C3 perfluoroalkylsulfonyl group;
In the formula (1), compounds wherein $R^3$ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group;
In the formula (1), compounds wherein $R^3$ is a C1 to C3 perfluoroalkyl group or a C1 to C3 perfluoroalkylsulfanyl group;
In the formula (1), compounds wherein $R^3$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (1), compounds wherein n is 0;
In the formula (1), compounds wherein n is 1;
In the formula (1), compounds wherein n is 2;
A Compound Represented by Formula (1)
wherein
$A^1$ is —$NR^4$—, a sulfur atom or an oxygen atom,
$A^2$ is a nitrogen atom or =CH—,
$R^1$ is an ethyl group, a cyclopropyl group or a cyclopropylmethyl group,
$R^2$ is —$S(O)_mCF_3$ or —$C(R^7)(CF_3)_2$,
$R^3$ is a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group,
$R^4$ is a methyl group,
$R^6$ is a C1 to C3 haloalkyl group, and
$R^7$ is a fluorine atom or a chlorine atom;
A Compound Represented by Formula (1)
wherein
$A^1$ is —$NR^4$—, a sulfur atom or an oxygen atom,
$A^2$ is a nitrogen atom or =CH—,
$R^1$ is an ethyl group, a cyclopropyl group or a cyclopropylmethyl group,
$R^2$ is —$S(O)_mCF_3$ or —$C(R^7)(CF_3)_2$,
$R^3$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group,
$R^4$ is a methyl group,
$R^6$ is a C1 to C3 haloalkyl group, and
$R^7$ is a fluorine atom or a chlorine atom;
A Compound Represented by Formula (1),
wherein
$A^1$ is —$NR^4$—,
$A^2$ is a nitrogen atom,
$R^1$ is an ethyl group, a cyclopropyl group or a cyclopropylmethyl group,
$R^2$ is —$S(O)_mR^6$ or —$C(R^7)(CF_3)_2$,
$R^3$ is a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group,
$R^4$ is a C1 to C6 alkyl group optionally having one or more halogen atoms,
$R^6$ is a C1 to C3 haloalkyl group,
$R^7$ is a fluorine atom,
m is 0, 1, or 2, and n is 0, 1, or 2.
A Compound Represented by Formula (1),
wherein
$A^1$ is —$NR^4$—,
$A^2$ is a nitrogen atom,
$R^1$ is an ethyl group, a cyclopropyl group or a cyclopropylmethyl group,
$R^2$ is —$S(O)_mR^6$ or —$CF(CF_3)_2$,
$R^3$ is a C1 to C3 perfluoroalkyl group or a C1 to C3 perfluoroalkylsulfanyl group,
$R^4$ is a C1 to C6 alkyl group optionally having one or more halogen atoms,
$R^6$ is a C1 to C3 haloalkyl group,
$R^7$ is a fluorine atom,
m is 0, 1, or 2, and n is 0, 1, or 2.
A Compound Represented by Formula (1),
wherein
$A^1$ is —$NCH_3$—,
$A^2$ is a nitrogen atom,
$R^1$ is an ethyl group,
$R^2$ is —$S(O)_mCF_3$ or —$CF(CF_3)_2$,
$R^3$ is a trifluoromethyl group, a pentafluoroethyl group or a trifluoromethylsulfanyl group,
m is 0, 1, or 2, and n is 0, 1, or 2.
In the formula (1-1), compounds wherein $A^{2b}$ is a nitrogen atom, $R^{3b}$ is a C2 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, and $R^{4b}$ is a methyl group;
In the formula (1-1), compounds wherein $A^{2b}$ is a nitrogen atom, $R^{3b}$ is a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, and $R^{4b}$ is a methyl group;
In the formula (1-1), compounds wherein $A^{2b}$ is a nitrogen atom, $R^{3b}$ is a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, $R^{4b}$ is a methyl group, $R^{1b}$ is an ethyl group, and $R^{2b}$ is a trifluoromethylsulfanyl group, a trifluoromethylsulfinyl group, a trifluoromethylsulfonyl group or a heptafluoroisopropyl group;
In the formula (1-1), compounds wherein $A^{2b}$ is a nitrogen atom;
In the formula (1-1), compounds wherein $A^{2b}$ is =CH—;
In the formula (1-1), compounds wherein $R^{1b}$ is an ethyl group;
In the formula (1-1), compounds wherein $R^{1b}$ is a cyclopropyl group;
In the formula (1-1), compounds wherein $R^{1b}$ is a cyclopropylmethyl group;
In the formula (1-1), compounds wherein $R^{2b}$ is a trifluoromethylsulfanyl group, a trifluoromethylsulfinyl group, or a trifluoromethylsulfonyl group;
In the formula (1-1), compounds wherein $R^{2b}$ is a heptafluoroisopropyl group;
In the formula (1-1), compounds wherein $R^{3b}$ is a C1 to C3 perfluoroalkyl group;
In the formula (1-1), compounds wherein $R^{3b}$ is a C1 to C3 perfluoroalkoxy group;
In the formula (1-1), compounds wherein $R^{3b}$ is a C1 to C3 perfluoroalkylsulfanyl group, a C1 to C3 perfluoroalkylsulfinyl group, or a C1 to C3 perfluoroalkylsulfonyl group;
In the formula (1-1), compounds wherein $R^{3b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (1-1), compounds wherein $R^{4b}$ is a methyl group;

In the formula (1-1), compounds wherein $R^{4b}$ is a hydrogen atom;

In the formula (1-1), compounds wherein $A^{2b}$ is a nitrogen atom, $R^{3b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, and $R^{4b}$ is a methyl group;

In the formula (1-1), compounds wherein $A^{2b}$ is =CH—, $R^{3b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, and $R^{4b}$ is a methyl group;

In the formula (1-2), compounds wherein $A^{2b}$ is a nitrogen atom;

In the formula (1-2), compounds wherein $A^{2b}$ is =CH—;

In the formula (1-2), compounds wherein $R^{1b}$ is an ethyl group;

In the formula (1-2), compounds wherein $R^b$ is a cyclopropyl group;

In the formula (1-2), compounds wherein $R^{1b}$ is a cyclopropylmethyl group;

In the formula (1-2), compounds wherein $R^{2b}$ is a trifluoromethylsulfanyl group, a trifluoromethylsulfinyl group, or a trifluoromethylsulfonyl group;

In the formula (1-2), compounds wherein $R^{2b}$ is a heptafluoroisopropyl group;

In the formula (1-2), compounds wherein $R^{3b}$ is a C1 to C3 perfluoroalkyl group;

In the formula (1-2), compounds wherein $R^{3b}$ is a C1 to C3 perfluoroalkoxy group;

In the formula (1-2), compounds wherein $R^{3b}$ is a C1 to C3 perfluoroalkylsulfanyl group, a C1 to C3 perfluoroalkylsulfinyl group, or a C1 to C3 perfluoroalkylsulfonyl group;

In the formula (1-2), compounds wherein $R^3$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;

In the formula (1-2), compounds wherein $A^{2b}$ is a nitrogen atom, $R^3$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group;

In the formula (1-2), compounds wherein $A^{2b}$ is =CH—, $R^3$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group;

In the formula (1-3), compounds wherein $A^{2b}$ is a nitrogen atom;

In the formula (1-3), compounds wherein $A^{2b}$ is =CH—;

In the formula (1-3), compounds wherein $R^{1b}$ is an ethyl group;

In the formula (1-3), compounds wherein $R^{1b}$ is a cyclopropyl group;

In the formula (1-3), compounds wherein $R^{1b}$ is a cyclopropylmethyl group;

In the formula (1-3), compounds wherein $R^{2b}$ is a trifluoromethylsulfanyl group, a trifluoromethylsulfinyl group, or a trifluoromethylsulfonyl group;

In the formula (1-3), compounds wherein $R^{2b}$ is a heptafluoroisopropyl group;

In the formula (1-3), compounds wherein $R^{3b}$ is a C1 to C3 perfluoroalkyl group;

In the formula (1-3), compounds wherein $R^{3b}$ is a C1 to C3 perfluoroalkoxy group;

In the formula (1-3), compounds wherein $R^{3b}$ is a C1 to C3 perfluoroalkylsulfanyl group, a C1 to C3 perfluoroalkylsulfinyl group, or a C1 to C3 perfluoroalkylsulfonyl group;

In the formula (1-3), compounds wherein $R^{3b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;

In the formula (1-3), compounds wherein $A^{2b}$ is a nitrogen atom, $R^{3b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group;

In the formula (1-3), compounds wherein $A^{2b}$ is =CH—, $R^{3b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group;

Compounds Represented by Formula (2-1):

(2-1)

wherein
$A^{2c}$ is a nitrogen atom or =CH—,
$R^{3c}$ is a C2 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, and
$R^{4c}$ is a methyl group.

Compounds Represented by Formula (2-2):

(2-2)

wherein
$R^{3c}$ is a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group.

Compounds Represented by Formula (2-3):

(2-3)

wherein
$A^{2c}$ is a nitrogen atom or =CH—,
$R^{3c}$ is a C2 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group.

Formula (2)

$$\text{(2)}$$

In the formula (2), compounds wherein $A^{1a}$ is $-NR^{4a}-$, and $A^{2a}$ is a nitrogen atom;
In the formula (2), compounds wherein $A^{1a}$ is $-NR^{4a}-$, and $A^{2a}$ is $=CH-$;
In the formula (2), compounds wherein $A^{1a}$ is $-NR^{4}-$, $R^{4a}$ is a methyl group, and $A^{2a}$ is a nitrogen atom;
In the formula (2), compounds wherein $A^{1a}$ is $-NR^{4}-$, $R^{4a}$ is a methyl group, and $A^{2a}$ is $=CH-$;
In the formula (2), compounds wherein $A^{1a}$ is an oxygen atom, and $A^{2a}$ is a nitrogen atom;
In the formula (2), compounds wherein $A^{1a}$ is an oxygen atom, and $A^{2a}$ is $=CH-$;
In the formula (2), compounds wherein $A^{1a}$ is a sulfur atom, and $A^{2a}$ is a nitrogen atom;
In the formula (2), compounds wherein $A^{1a}$ is a sulfur atom, and $A^{2a}$ is $=CH-$;
In the formula (2), compounds wherein $R^{3a}$ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group;
In the formula (2), compounds wherein $R^{3a}$ is a C2 to C3 perfluoroalkyl group, a C1 to C3 perfluoroalkylsulfanyl group, a C1 to C3 perfluoroalkylsulfinyl group, or a C1 to C3 perfluoroalkylsulfonyl group;
In the formula (2), compounds wherein $R^{3a}$ is a C2 to C3 perfluoroalkyl group;
In the formula (2), compounds wherein $R^{3a}$ is a C1 to C3 perfluoroalkylsulfanyl group, a C1 to C3 perfluoroalkylsulfinyl group, or a C1 to C3 perfluoroalkylsulfonyl group;
In the formula (2), compounds wherein $R^{3a}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2), compounds wherein $R^{3a}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2), compounds wherein $R^{3a}$ is a pentafluoroethyl group, a trifluoromethylsulfanyl group, a trifluoromethylsulfinyl group, or a trifluoromethylsulfonyl group;
In the formula (2), compounds wherein
  $A^{1a}$ is $-NR^{4a}-$,
  $A^{2a}$ is a nitrogen atom,
  $R^{3a}$ is a C1 to C3 perfluoroalkyl group or a C1 to C3 perfluoroalkylsulfanyl group, and
  $R^{4a}$ is a C1 to C3 alkyl group optionally having one or more halogen atoms.
In the formula (2), compounds wherein
  $A^{1a}$ is $-NCH_3-$,
  $A^{2a}$ is a nitrogen atom, and
  $R^{3a}$ is a C1 to C3 perfluoroalkyl group or a C1 to C3 perfluoroalkylsulfanyl group.
In the formula (2), compounds wherein
  $A^{1a}$ is $-NCH_3-$,
  $A^{2a}$ is a nitrogen atom, and
  $R^{3a}$ is a trifluoromethyl group, a pentafluoroethyl group or a trifluoromethylsulfanyl group.

In the formula (2-1), compounds wherein $A^{2c}$ is a nitrogen atom;
In the formula (2-1), compounds wherein $A^{2c}$ is $=CH-$;
In the formula (2-1), compounds wherein $R^{3c}$ is a C2 to C3 perfluoroalkyl group;
In the formula (2-1), compounds wherein $R^{3c}$ is a C1 to C3 perfluoroalkylsulfanyl group, a C1 to C3 perfluoroalkylsulfinyl group, or a C1 to C3 perfluoroalkylsulfonyl group;
In the formula (2-1), compounds wherein $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2-1), compounds wherein $R^{3c}$ is a pentafluoroethyl group, a trifluoromethylsulfanyl group, a trifluoromethylsulfinyl group, or a trifluoromethylsulfonyl group;
In the formula (2-1), compounds wherein $A^{2c}$ is a nitrogen atom, and $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2-1), compounds wherein $A^{2c}$ is $=CH-$, and $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2-1), compounds wherein $A^{2c}$ is a nitrogen atom, $R^{3c}$ is a C2 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, and $R^{4c}$ is a methyl group;
In the formula (2-1), compounds wherein $A^{2c}$ is a nitrogen atom, $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, and $R^{4c}$ is a methyl group;
In the formula (2-2), compounds wherein $R^{3c}$ is a C1 to C3 perfluoroalkyl group;
In the formula (2-2), compounds wherein $R^{3c}$ is a C1 to C3 perfluoroalkylsulfanyl group, a C1 to C3 perfluoroalkylsulfinyl group, or a C1 to C3 perfluoroalkylsulfonyl group;
In the formula (2-2), compounds wherein $R^{3c}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2-3), compounds wherein $A^{2c}$ is a nitrogen atom;
In the formula (2-3), compounds wherein $A^{2c}$ is $=CH-$;
In the formula (2-3), compounds wherein $R^{3c}$ is a C2 to C3 perfluoroalkyl group;
In the formula (2-3), compounds wherein $R^{3c}$ is a C1 to C3 perfluoroalkylsulfanyl group, a C1 to C3 perfluoroalkylsulfinyl group, or a C1 to C3 perfluoroalkylsulfonyl group;
In the formula (2-3), compounds wherein $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;
In the formula (2-3), compounds wherein $R^{3c}$ is a pentafluoroethyl group, a trifluoromethylsulfanyl group, a trifluoromethylsulfinyl group, or a trifluoromethylsulfonyl group;
In the formula (2-3), compounds wherein $A^{2c}$ is a nitrogen atom, and $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group;

In the formula (2-3), compounds wherein $A^{2c}$ is =CH—, and $R^{3c}$ is a pentafluoroethyl group, a heptafluoropropyl group, a heptafluoroisopropyl group, a trifluoromethoxy group, a trifluoromethylsulfanyl group, a trifluoromethylsulfinyl group, or a trifluoromethylsulfonyl group.

Next, the method for producing the compound of the present invention will be described.

The compound of the present invention and an intermediate compound can be produced, for example, according to the following (Production Method 1) to (Production Method 12).

(Production Method 1)

The compound of the present invention in which n is 1 or 2 in the formula (1) can be produced by oxidizing the compound of the present invention in which n is 0:

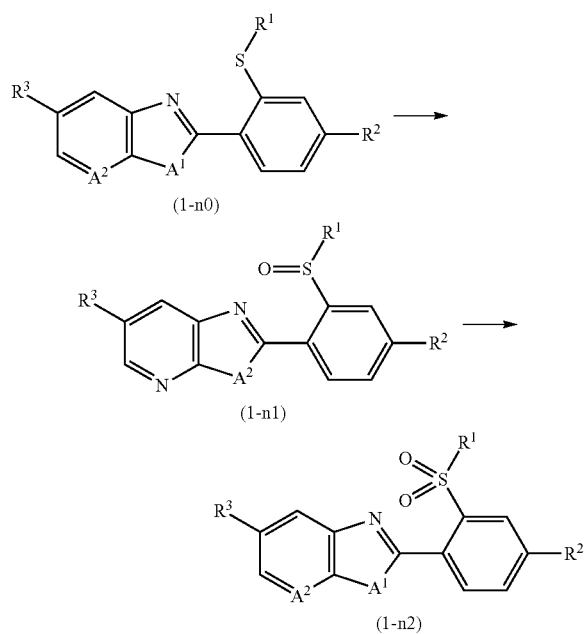

wherein symbols represent the same meaning as described above.

The compound of the present invention (1-n1) in which n is 1 in the formula (1) can be produced by oxidizing the compound of the present invention (1-n0) in which n is 0.

The oxidation reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperbenzoic acid.

In the reaction, the oxidizing agent is usually used in a ratio of 1 to 3 mol, based on 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of −20 to 80° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n1) can be isolated. The isolated compound of the present invention (1-n1) also can be further purified by chromatography, recrystallization, or the like.

The compound of the present invention (1-n2) in which n is 2 in the formula (1) can be produced by reacting the compound of the present invention (1-n1) in which n is 1 with an oxidizing agent.

The oxidation reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 1 to 4 mol, based on 1 mol of the compound of the present invention (1-n1). Preferably, the oxidizing agent is used in a ratio of 1 to 2 mol, based on 1 mol of the compound of the present invention (1-n1).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n2) can be isolated. The compound of the present invention (1-n2) also can be further purified by chromatography, recrystallization, or the like.

The compound of the present invention (1-n2) in which n is 2 in the formula (1) can be produced by a one step reaction (one pot) by oxidizing the compound of the present invention (1-n0) in which n is 0.

The oxidation reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide. The reaction can be also carried out, in the presence of a catalyst, as necessary. Examples of the catalyst include sodium tungstate.

In the reaction, the oxidizing agent is usually used in a ratio of 2 to 5 mol, and the catalyst is usually used in a ratio of 0.01 to 0.5 mol, based on 1 mol of the compound of the present invention (1-n0). Preferably, the oxidizing agent is used in a ratio of 2 to 3 mol, based on 1 mol of the compound of the present invention (1-n0).

The reaction temperature is usually within the range of 0 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n2) can be isolated. The isolated compound of the present invention (1-n2) also can be further purified by chromatography, recrystallization, or the like.

(Production Method 2)

The compound of the present invention (1-n0) in which n is 0 in the formula (1) can be produced by reacting the intermediate compound (M1) with the intermediate compound (M2), in the presence of a base:

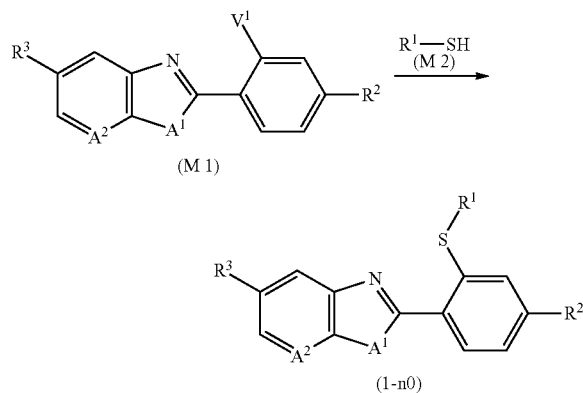

wherein $V^1$ represents a fluorine atom or a chlorine atom, and other symbols represent the same meaning as described above.

The reaction is usually carried out in the presence of a solvent.

Examples of the solvent include ethers such as tetrahydrofuran (hereinafter, referred to as THF), ethylene glycol dimethyl ether, tert-butyl methyl ether and 1,4-dioxane, aromatic hydrocarbons such as toluene and xylene, nitriles such as acetonitrile, aprotic polar solvents such as N,N-dimethylformamide (hereinafter, referred to as DMF), N-methyl pyrrolidone (hereinafter, referred to as NMP) and dimethyl sulfoxide (hereinafter, referred to as DMSO), water, and mixtures thereof.

Examples of the base include alkali metal carbonates such as sodium carbonate and potassium carbonate, and alkali metal hydrides such as sodium hydride.

In the reaction, the intermediate compound (M2) is usually used in a ratio of 1 to 10 mol, and the base is usually used in a ratio of 1 to 10 mol, based on 1 mol of the intermediate compound (M1).

The reaction temperature is usually within the range of 0 to 150° C. The reaction time is usually within the range of 0.5 to 24 hours.

After completion of the reaction, the reaction mixture is extracted with an organic solvent, and the organic layer is subjected to post-treatment operations such as drying and concentration, whereby the compound of the present invention (1-n0) in which n is 0 can be isolated. The isolated compound of the present invention (1-n0) in which n is 0 also can be further purified by chromatography, recrystallization, or the like.

(Production Method 3)

The compound of the present invention (1-n0) in which n is 0 in the formula (1) can be produced by reacting the intermediate compound (M3) or the intermediate compound (M4) that is a disulfide body thereof with the intermediate compound (M5), in the presence of a base:

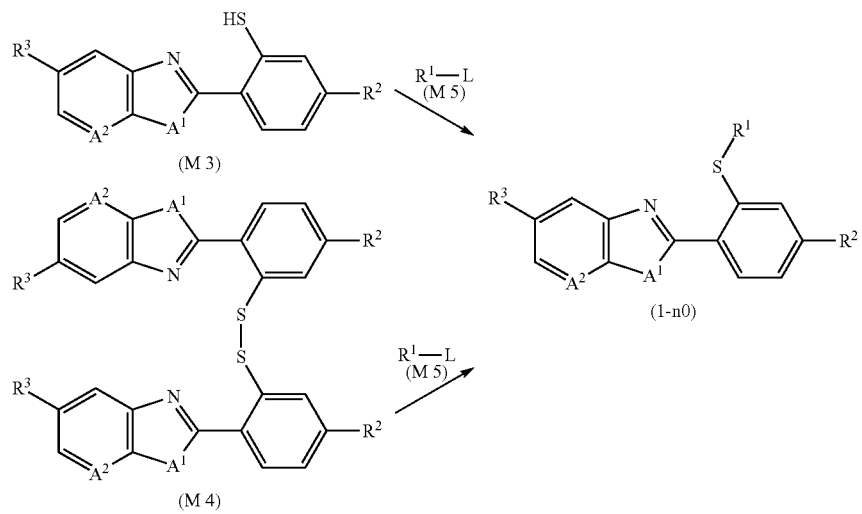

wherein L represents a leaving group such as a chlorine atom, a bromine atom, an iodine atom, a trifluoromethanesulfonyloxy group or a methanesulfonyloxy group, and other symbols represent the same meaning as described above.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

When the intermediate compound (M4) that is a disulfide body is used, the reaction is usually carried out in the presence of a reducing agent. Examples of the reducing agent include sodium hydroxymethanesulfinate (trade name: Rongalite).

In the reaction, the intermediate compound (M5) is usually used in a ratio of 1 to 10 mol, and the base is usually used in a ratio of 1 to 10 mol, based on 1 mol of the intermediate compound (M3). Also, when the intermediate compound (M4) that is a disulfide body is used, the intermediate compound (M5) is usually used in a ratio of 2 to 10 mol, the base is usually used in a ratio of 2 to 10 mol, and the reducing agent is usually used in a ratio of 1 to 5 mol, based on 1 mol of the intermediate compound (M4).

The reaction temperature is usually within the range of 0 to 100° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (1-n0) in which n is 0 can be isolated. The isolated compound of the present invention (1-n0) in which n is 0 also can be further purified by chromatography, recrystallization, or the like.

(Production Method 4)

The compound of the present invention (P2) in which $A^1$ is —$NR^{4'}$— can be produced by reacting the compound of the present invention (P1) in which $A^1$ is —NH— with the intermediate compound (M6), in the presence of a base:

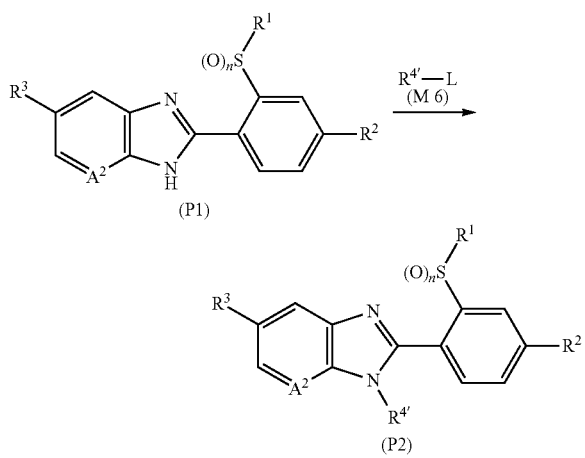

wherein $R^{4'}$ represents a C1 to C6 alkyl group optionally having one or more atoms or groups selected from halogen atoms and a cyclopropyl group or a C3 to C6 cycloalkyl group optionally having one or more atoms or groups selected from halogen atoms and C1 to C3 alkyl groups, and other symbols represent the same meaning as described above.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

In the reaction, the intermediate compound (M6) is usually used in a ratio of 1 to 5 mol, and the base is usually used in a ratio of 1 to 3 mol, based on 1 mol of the compound of the present invention (P1).

The reaction temperature is usually within the range of 0 to 100° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (P2) can be isolated. The isolated compound of the present invention (P2) also can be further purified by chromatography, recrystallization, or the like.

(Production Method 5)

The compound of the present invention (1) can be produced by reacting the intermediate compound (M7) with the intermediate compound (M8), in the presence of a palladium catalyst, a copper catalyst, a ligand and a base:

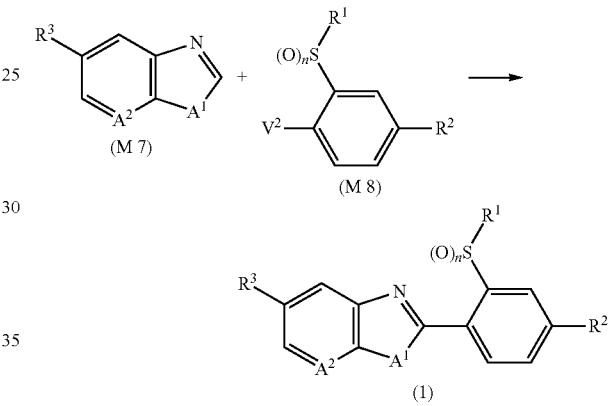

wherein $V^2$ represents a bromine atom or a iodine atom, and other symbols represent the same meaning as described above.

The reaction is usually carried out in the presence of a solvent.

Examples of the solvent include aromatic hydrocarbons such as toluene and xylene, ethers such as THF, ethylene glycol dimethyl ether, tert-butyl methyl ether and 1,4-dioxane, aprotic polar solvents such as DMF, NMP and DMSO, and mixtures thereof.

The palladium catalyst includes palladium(II) acetate.

Examples of the copper catalyst include copper(II) acetate, copper(II) acetate monohydrate, and copper(I) iodide.

Examples of the ligand include triphenylphosphine and tricyclohexylphosphine.

Examples of the base include inorganic bases such as sodium carbonate, potassium carbonate and cesium carbonate.

In the reaction, the intermediate compound (M8) is usually used in a ratio of 0.8 to 5 mol, the palladium catalyst is usually used in a ratio of 0.01 to 0.3 mol, the copper catalyst is usually used in a ratio of 0.01 to 0.3 mol, the ligand is usually used in a ratio of 0.02 to 1 mol, and the base is usually used in a ratio of 1 to 5 mol, based on 1 mol of the intermediate compound (M7).

The reaction temperature is usually within the range of 0 to 200° C. The reaction time is usually within the range of 0.1 to 48 hours.

After completion of the reaction, the reaction mixture is extracted with an organic solvent, and the organic layer is subjected to post-treatment operations such as drying and concentration, whereby the compound of the present invention (1) can be isolated. The isolated compound of the present invention (1) also can be further purified by chromatography, recrystallization, or the like.

(Production Method 6)

The intermediate compound (M1) can be produced by reacting the intermediate compound (M7) with the intermediate compound (M9), in the presence of a palladium catalyst, a copper catalyst, a ligand and a base:

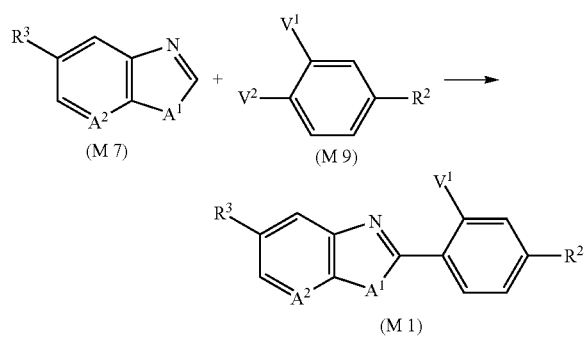

wherein symbols represent the same meaning as described above.

The reaction is usually carried out in the presence of a solvent.

Examples of the solvent include aromatic hydrocarbons such as toluene and xylene, ethers such as THF, ethylene glycol dimethyl ether, tert-butyl methyl ether and 1,4-dioxane, aprotic polar solvents such as DMF, NMP and DMSO, and mixtures thereof.

Examples of the palladium catalyst include palladium(II) acetate.

Examples of the copper catalyst include copper(II) acetate, copper(II) acetate monohydrate, and copper(I) iodide.

Examples of the ligand include triphenylphosphine and tricyclohexylphosphine.

Examples of the base include inorganic bases such as sodium carbonate, potassium carbonate and cesium carbonate.

In the reaction, the intermediate compound (M9) is usually used in a ratio of 0.8 to 2 mol, the palladium catalyst is usually used in a ratio of 0.05 to 0.2 mol, the copper catalyst is usually used in a ratio of 0.1 to 0.3 mol, the ligand is usually used in a ratio of 0.1 to 1 mol, and the base is usually used in a ratio of 1 to 5 mol, based on 1 mol of the intermediate compound (M7).

The reaction temperature is usually within the range of 20 to 180° C. The reaction time is usually within the range of 0.1 to 20 hours.

After completion of the reaction, the reaction mixture is extracted with an organic solvent, and the organic layer is subjected to post-treatment operations such as drying and concentration, whereby the intermediate compound (M1) can be isolated. The isolated intermediate compound (M1) also can be further purified by chromatography, recrystallization, or the like.

(Production Method 7)

The intermediate compound (M10) in which n is 0 in the intermediate compound (M8) can be produced by reacting the intermediate compound (M9) with the intermediate compound (M2), in the presence of a base. In addition, the intermediate compound (M8) in which n is 1 or 2 can be produced by oxidizing the intermediate compound (M10) in which n is 0:

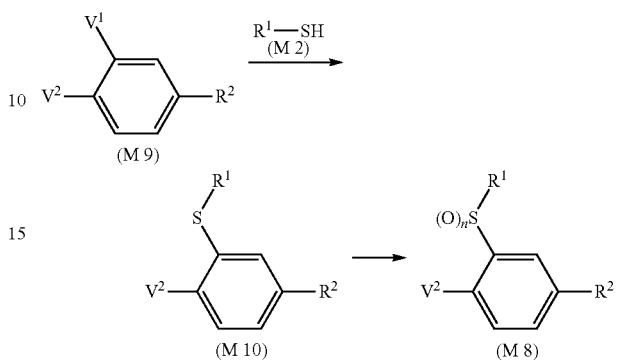

wherein symbols represent the same meaning as described above.

The intermediate compound (M10) can be produced by reacting the intermediate compound (M9) with the intermediate compound (M2), in the presence of a base.

The reaction is usually carried out in the presence of a solvent.

Examples of the solvent include aromatic hydrocarbons such as toluene and xylene, ethers such as THF, ethylene glycol dimethyl ether, tert-butyl methyl ether and 1,4-dioxane, aprotic polar solvents such as DMF, NMP and DMSO, water, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

In the reaction, the intermediate compound (M2) is usually used in a ratio of 0.8 to 1.2 mol, and the base is usually used in a ratio of 1 to 2 mol, based on 1 mol of the intermediate compound (M9).

The reaction temperature is usually within the range of 0 to 200° C. The reaction time is usually within the range of 0.1 to 24 hours.

After completion of the reaction, the reaction mixture is extracted with an organic solvent, and the organic layer is subjected to post-treatment operations such as drying and concentration, whereby the intermediate compound (M10) can be isolated. The isolated intermediate compound (M10) also can be further purified by chromatography, recrystallization, or the like.

The intermediate compound (M8) in which n is 1 or 2 can be produced by oxidizing the intermediate compound (M10).

The intermediate compound (M10) in which n is 1 or 2 can be produced, using the intermediate compound (M10) in place of the compound of the present invention (1-n0), in accordance with the method of Production Method 1.

(Production Method 8)

The intermediate compound (M7) can be produced by reacting the intermediate compound (M11) with a formylating agent:

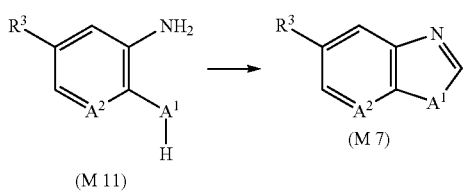

(M 11)   (M 7)

wherein symbols represent the same meaning as described above.

The formylation reaction is usually carried out in the presence of a solvent.

Examples of the solvent include alcohols such as methanol and ethanol, aromatic hydrocarbons such as toluene and xylene, ethers such as THF, ethylene glycol dimethyl ether, tert-butyl methyl ether and 1,4-dioxane, aprotic polar solvents such as DMF, NMP and DMSO, water, and mixtures thereof. In addition, the reaction can be carried out using a formylating agent as the solvent.

Examples of the formylating agent include formic acid, methyl orthoformate, and ethyl orthoformate.

The reaction can be also carried out by adding an acid, as necessary. Examples of the acid include mineral acids such as hydrochloric acid and sulfuric acid, and p-toluenesulfonic acid.

In the reaction, the formylating agent is usually used in a ratio of 1 to 10 mol, and the acid is usually used in a ratio of 0.01 to 0.5 mol, based on 1 mol of the intermediate compound (M11).

The reaction temperature is usually within the range of 0 to 200° C. The reaction time is usually within the range of 0.1 to 24 hours.

After completion of the reaction, the reaction mixture is extracted with an organic solvent, and the organic layer is subjected to post-treatment operations such as drying and concentration, whereby the intermediate compound (M7) can be isolated. The isolated intermediate compound (M7) also can be further purified by chromatography, recrystallization, or the like.

(Production Method 9)

The intermediate compound (M11) can be produced, for example, according to the following method:

(M 12)   (M 13)

(M 11)

wherein symbols represent the same meaning as described above.

The intermediate compound (M13) can be produced by reacting the intermediate compound (M12) with a nitrating agent.

The reaction is usually carried out in the presence of a solvent.

Examples of the solvent include halogenated hydrocarbons such as chloroform, acetic acid, concentrated sulfuric acid, concentrated nitric acid, water, and mixtures thereof.

Examples of the nitrating agent used in the reaction include concentrated nitric acid.

In the reaction, the nitrating agent is usually used in a ratio of 1 to 3 mol, based on 1 mol of the intermediate compound (M12).

The reaction temperature is usually within the range of −10 to 100° C., and the reaction time is usually within the range of 0.1 to 24 hours.

After completion of the reaction, the intermediate compound (M13) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated intermediate compound (M13) can be also further purified by recrystallization, chromatography, or the like.

The intermediate compound (M11) can be produced by reacting the intermediate compound (M13) with hydrogen, in the presence of a hydrogenation catalyst.

The reaction is carried out in the presence of a solvent, usually in a hydrogen atmosphere of 1 to 100 atmospheric pressure.

Examples of the solvent include ethers such as THF and 1,4-dioxane, esters such as ethyl acetate and butyl acetate, alcohols such as methanol and ethanol, water, and mixtures thereof.

Examples of the hydrogenation catalyst include transition metal compounds such as palladium-carbon, palladium hydroxide, Raney (registered trademark) nickel and platinum oxide.

In the reaction, the hydrogen is usually used in a ratio of 3 mol, and the hydrogenation catalyst is usually used in a ratio of 0.001 to 0.5 mol, based on 1 mol of the intermediate compound (M13).

The reaction temperature is usually within the range of −20 to 100° C., and the reaction time is usually within the range of 0.1 to 24 hours.

After completion of the reaction, the intermediate compound (M11) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated intermediate compound (M11) can be also further purified by recrystallization, chromatography, or the like.

(Production Method 10)

The intermediate compound (M11) in which $A^1$ is $NR^4$ and $A^2$ is a nitrogen atom can be produced, for example, according to the following method:

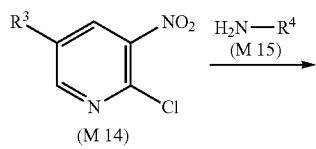

(M 14)

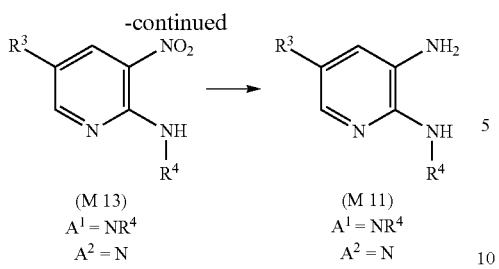 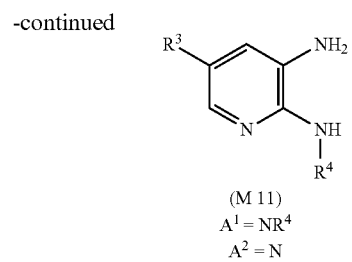

(M 13)
$A^1 = NR^4$
$A^2 = N$ (M 11)
$A^1 = NR^4$
$A^2 = N$ (M 11)
$A^1 = NR^4$
$A^2 = N$ wherein symbols represent the same meaning as in the formula (1).

The intermediate compound (M13) in which $A^1$ is $NR^4$ and $A^2$ is a nitrogen atom can be produced by reacting the intermediate compound (M14) with the intermediate compound (M15), in the presence of a base.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

The reaction can be also carried out by adding a base, as necessary.

Examples of the base include alkali metal hydrides such as sodium hydride, alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M15) is usually used in a ratio of 1 to 10 mol, and the base is usually used in a ratio of 1 to 10 mol, based on 1 mol of the intermediate compound (M14).

The reaction temperature is usually within the range of 0 to 150° C. The reaction time is usually within the range of 0.5 to 24 hours.

After completion of the reaction, the reaction mixture is extracted with an organic solvent, and the organic layer is subjected to post-treatment operations such as drying and concentration, whereby the intermediate compound (M13) in which $A^1$ is $NR^4$ and $A^2$ is a nitrogen atom can be isolated. The isolated intermediate compound (M13) in which $A^1$ is $NR^4$ and $A^2$ is a nitrogen atom also can be further purified by chromatography, recrystallization, or the like.

The intermediate compound (M11) in which $A^1$ is $NR^4$ and $A^2$ is a nitrogen atom can be produced, using the intermediate compound (M13) in which $A^1$ is $NR^4$ and $A^2$ is a nitrogen atom in place of the intermediate compound (M13), in accordance with the method of Production Method 9.

(Production Method 11)

The intermediate compound (M11) in which $A^1$ is $NR^4$ and $A^2$ is a nitrogen atom can be produced, for example, according to the following method:

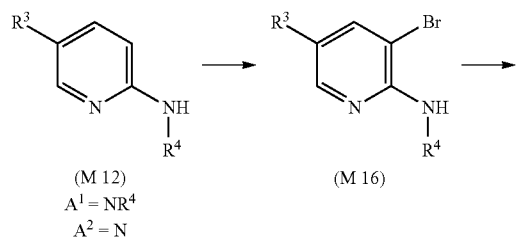

(M 12)
$A^1 = NR^4$
$A^2 = N$ (M 16)

wherein symbols represent the same meaning as in the formula (1).

The intermediate compound (M16) can be produced by reacting the intermediate compound (M12) in which $A^1$ is $NR^4$ and $A^2$ is a nitrogen atom with a brominating agent.

The reaction is usually carried out in the presence of a solvent.

Examples of the solvent include water, acetic acid, ethers such as 1,4-dioxane, diethyl ether and THF, esters such as ethyl acetate and butyl acetate, halogenated hydrocarbons such as dichloromethane, chloroform, carbon tetrachloride and 1,2-dichloroethane, nitriles such as acetonitrile, aprotic polar solvents such as DMF, NMP and DMSO, and mixtures thereof.

Examples of the brominating agent include N-bromosuccinimide and bromine.

In the reaction, the brominating agent is usually used in a ratio of 1 to 3 mol, based on 1 mol of the intermediate compound (M12) in which $A^1$ is $NR^4$ and $A^2$ is a nitrogen atom.

The reaction temperature is usually within the range of −10 to 100° C., and the reaction time is usually within the range of 0.1 to 24 hours.

After completion of the reaction, the intermediate compound (M16) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated intermediate compound (M16) can be also further purified by recrystallization, chromatography, or the like.

The intermediate compound (M11) in which $A^1$ is $NR^4$ and $A^2$ is a nitrogen atom can be produced by reacting the intermediate compound (M16) with an aminating agent, in the presence of copper or a copper compound.

The reaction is usually carried out in the presence of a solvent.

Examples of the solvent used in the reaction include water, alcohols such as methanol and ethanol, ethers such as 1,4-dioxane, diethyl ether and THF, esters such as ethyl acetate and butyl acetate, halogenated hydrocarbons such as dichloromethane, chloroform, carbon tetrachloride and 1,2-dichloroethane, nitriles such as acetonitrile, aprotic polar solvents such as DMF, NMP, and DMSO, nitrogen-containing aromatic compounds such as pyridine and quinoline, and mixtures thereof.

Examples of the aminating agent used in the reaction include ammonia, aqueous ammonia, and lithium amide.

Examples of the copper compound include copper(I) iodide, copper(I) oxide, copper(II) oxide, acetylacetone copper(II), copper(II) acetate, and copper(II) sulfate.

The reaction can be also carried out by adding a ligand as necessary. Examples of the ligand include acetylacetone, salen, phenanthroline, and the like.

The reaction can be also carried out by adding a base, as necessary.

Examples of the base used in the reaction include nitrogen-containing heterocyclic compounds such as pyridine, picoline, 2,6-lutidine, diazabicycloundecene (hereinafter, referred to as DBU) and 1,5-diazabicyclo[4.3.0]-5-nonene, tertiary amines such as triethylamine and N,N-diisopropylethylamine, and inorganic bases such as tripotassium phosphate, potassium carbonate, cesium carbonate and sodium hydroxide.

In the reaction, the aminating agent is usually used in a ratio of 1 to 5 mol, copper or the copper compound is usually used in a ratio of 0.02 to 0.5 mol, the ligand is usually used in a ratio of 0.02 to 2 mol, and the base is usually used in a ratio of 1 to 5 mol, based on 1 mol of the intermediate compound (M16).

The reaction temperature is usually within the range of 30 to 200° C., and the reaction time is usually within the range of 0.1 to 48 hours.

After completion of the reaction, the intermediate compound (M11) in which $A^1$ is $NR^4$ and $A^2$ is a nitrogen atom can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated intermediate compound (M11) in which $A^1$ is $NR^4$ and $A^2$ is a nitrogen atom also can be further purified by recrystallization, chromatography, or the like.

(Production Method 12)

The intermediate compound (M11) in which $A^1$ is a sulfur atom and $A^2$ is a nitrogen atom can be produced, for example, according to the following method:

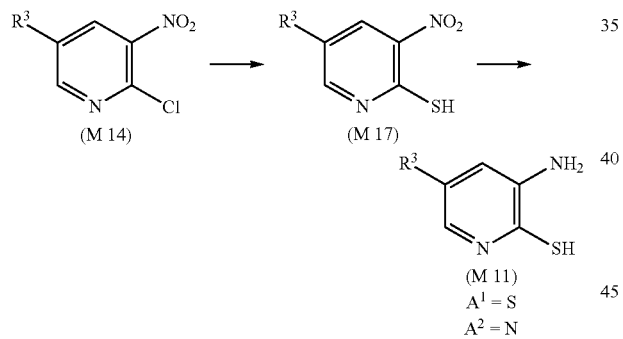

wherein symbols represent the same meaning as in the formula (1).

The intermediate compound (M17) can be produced by reacting the intermediate compound (M14) with thiourea, in the presence of a base.

The reaction is usually carried out in the presence of a solvent.

Examples of the solvent include alcohols such as methanol and ethanol, water, and mixtures thereof.

Examples of the base include alkali metal hydroxides such as sodium hydroxide and potassium hydroxide.

In the reaction, thiourea is usually used in a ratio of 0.5 to 3 mol, and the base is usually used in a ratio of 1 to 10 mol, based on 1 mol of the intermediate compound (M14).

The reaction temperature is usually within the range of 0 to 100° C. The reaction time is usually within the range of 0.1 to 24 hours.

After completion of the reaction, an acid is added to the reaction mixture, and then the mixture is extracted with an organic solvent, and the organic layer is subjected to post-treatment operations such as drying and concentration, whereby the intermediate compound (M17) can be isolated. The isolated intermediate compound (M17) also can be further purified by chromatography, recrystallization, or the like.

The intermediate compound (M11) in which $A^1$ is a sulfur atom and $A^2$ is a nitrogen atom can be produced, using the intermediate compound (M13) in which $A^1$ is a sulfur atom and $A^2$ is a nitrogen atom in place of the intermediate compound (M13), in accordance with the method of Production Method 9.

Next, specific examples of the compound of the present invention are shown below.

In the formula (1):

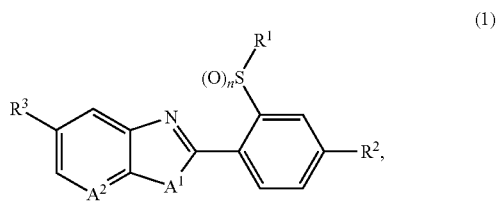

compounds wherein $R^2$ is a trifluoromethylsulfanyl group, and $R^3$ is a trifluoromethyl group, $R^1$, $A^1$, $A^2$ and n are the combinations shown in [Table 1] to [Table 16].

TABLE 1

| $R^1$ | $A^1$ | $A^2$ | n |
|---|---|---|---|
| Me | NMe | CH | 0 |
| Me | NMe | CH | 1 |
| Me | NMe | CH | 2 |
| Et | NMe | CH | 0 |
| Et | NMe | CH | 1 |
| Et | NMe | CH | 2 |
| Pr | NMe | CH | 0 |
| Pr | NMe | CH | 1 |
| Pr | NMe | CH | 2 |
| iPr | NMe | CH | 0 |
| iPr | NMe | CH | 1 |
| iPr | NMe | CH | 2 |
| tBu | NMe | CH | 0 |
| tBu | NMe | CH | 1 |
| tBu | NMe | CH | 2 |
| $CF_3$ | NMe | CH | 0 |
| $CF_3$ | NMe | CH | 1 |
| $CF_3$ | NMe | CH | 2 |
| $CH_2CF_3$ | NMe | CH | 0 |
| $CH_2CF_3$ | NMe | CH | 1 |
| $CH_2CF_3$ | NMe | CH | 2 |
| $CH=CH_2$ | NMe | CH | 0 |
| $CH=CH_2$ | NMe | CH | 1 |
| $CH=CH_2$ | NMe | CH | 2 |

TABLE 2

| $R^1$ | $A^1$ | $A^2$ | n |
|---|---|---|---|
| $CH_2CH=CH_2$ | NMe | CH | 0 |
| $CH_2CH=CH_2$ | NMe | CH | 1 |
| $CH_2CH=CH_2$ | NMe | CH | 2 |
| C≡CH | NMe | CH | 0 |
| C≡CH | NMe | CH | 1 |
| C≡CH | NMe | CH | 2 |
| $CH_2C≡CH$ | NMe | CH | 0 |
| $CH_2C≡CH$ | NMe | CH | 1 |
| $CH_2C≡CH$ | NMe | CH | 2 |
| CycPr | NMe | CH | 0 |

TABLE 2-continued

| R¹ | A¹ | A² | n |
|---|---|---|---|
| CycPr | NMe | CH | 1 |
| CycPr | NMe | CH | 2 |
| CH₂CycPr | NMe | CH | 0 |
| CH₂CycPr | NMe | CH | 1 |
| CH₂CycPr | NMe | CH | 2 |

TABLE 3

| R¹ | A¹ | A² | n |
|---|---|---|---|
| Me | NMe | N | 0 |
| Me | NMe | N | 1 |
| Me | NMe | N | 2 |
| Et | NMe | N | 0 |
| Et | NMe | N | 1 |
| Et | NMe | N | 2 |
| Pr | NMe | N | 0 |
| Pr | NMe | N | 1 |
| Pr | NMe | N | 2 |
| iPr | NMe | N | 0 |
| iPr | NMe | N | 1 |
| iPr | NMe | N | 2 |
| tBu | NMe | N | 0 |
| tBu | NMe | N | 1 |
| tBu | NMe | N | 2 |
| CF₃ | NMe | N | 0 |
| CF₃ | NMe | N | 1 |
| CF₃ | NMe | N | 2 |
| CH₂CF₃ | NMe | N | 0 |
| CH₂CF₃ | NMe | N | 1 |
| CH₂CF₃ | NMe | N | 2 |
| CH=CH₂ | NMe | N | 0 |
| CH=CH₂ | NMe | N | 1 |
| CH=CH₂ | NMe | N | 2 |

TABLE 4

| R¹ | A¹ | A² | n |
|---|---|---|---|
| CH₂CH=CH₂ | NMe | N | 0 |
| CH₂CH=CH₂ | NMe | N | 1 |
| CH₂CH=CH₂ | NMe | N | 2 |
| C≡CH | NMe | N | 0 |
| C≡CH | NMe | N | 1 |
| C≡CH | NMe | N | 2 |
| CH₂C≡CH | NMe | N | 0 |
| CH₂C≡CH | NMe | N | 1 |
| CH₂C≡CH | NMe | N | 2 |
| CycPr | NMe | N | 0 |
| CycPr | NMe | N | 1 |
| CycPr | NMe | N | 2 |
| CH₂CycPr | NMe | N | 0 |
| CH₂CycPr | NMe | N | 1 |
| CH₂CycPr | NMe | N | 2 |

TABLE 5

| R¹ | A¹ | A² | n |
|---|---|---|---|
| Me | NH | CH | 0 |
| Me | NH | CH | 1 |
| Me | NH | CH | 2 |
| Et | NH | CH | 0 |
| Et | NH | CH | 1 |
| Et | NH | CH | 2 |
| Pr | NH | CH | 0 |
| Pr | NH | CH | 1 |
| Pr | NH | CH | 2 |
| iPr | NH | CH | 0 |
| iPr | NH | CH | 1 |
| iPr | NH | CH | 2 |
| tBu | NH | CH | 0 |
| tBu | NH | CH | 1 |
| tBu | NH | CH | 2 |
| CF₃ | NH | CH | 0 |
| CF₃ | NH | CH | 1 |
| CF₃ | NH | CH | 2 |
| CH₂CF₃ | NH | CH | 0 |
| CH₂CF₃ | NH | CH | 1 |
| CH₂CF₃ | NH | CH | 2 |
| CH=CH₂ | NH | CH | 0 |
| CH=CH₂ | NH | CH | 1 |
| CH=CH₂ | NH | CH | 2 |

TABLE 6

| R¹ | A¹ | A² | n |
|---|---|---|---|
| CH₂CH=CH₂ | NH | CH | 0 |
| CH₂CH=CH₂ | NH | CH | 1 |
| CH₂CH=CH₂ | NH | CH | 2 |
| C≡CH | NH | CH | 0 |
| C≡CH | NH | CH | 1 |
| C≡CH | NH | CH | 2 |
| CH₂C≡CH | NH | CH | 0 |
| CH₂C≡CH | NH | CH | 1 |
| CH₂C≡CH | NH | CH | 2 |
| CycPr | NH | CH | 0 |
| CycPr | NH | CH | 1 |
| CycPr | NH | CH | 2 |
| CH₂CycPr | NH | CH | 0 |
| CH₂CycPr | NH | CH | 1 |
| CH₂CycPr | NH | CH | 2 |

TABLE 7

| R¹ | A¹ | A² | n |
|---|---|---|---|
| Me | NH | N | 0 |
| Me | NH | N | 1 |
| Me | NH | N | 2 |
| Et | NH | N | 0 |
| Et | NH | N | 1 |
| Et | NH | N | 2 |
| Pr | NH | N | 0 |
| Pr | NH | N | 1 |
| Pr | NH | N | 2 |
| iPr | NH | N | 0 |
| iPr | NH | N | 1 |
| iPr | NH | N | 2 |
| tBu | NH | N | 0 |
| tBu | NH | N | 1 |
| tBu | NH | N | 2 |
| CF₃ | NH | N | 0 |
| CF₃ | NH | N | 1 |
| CF₃ | NH | N | 2 |
| CH₂CF₃ | NH | N | 0 |
| CH₂CF₃ | NH | N | 1 |
| CH₂CF₃ | NH | N | 2 |
| CH=CH₂ | NH | N | 0 |
| CH=CH₂ | NH | N | 1 |
| CH=CH₂ | NH | N | 2 |

TABLE 8

| R¹ | A¹ | A² | n |
|---|---|---|---|
| CH₂CH=CH₂ | NH | N | 0 |
| CH₂CH=CH₂ | NH | N | 1 |
| CH₂CH=CH₂ | NH | N | 2 |
| C≡CH | NH | N | 0 |
| C≡CH | NH | N | 1 |

TABLE 8-continued

| R¹ | A¹ | A² | n |
|---|---|---|---|
| C≡CH | NH | N | 2 |
| CH₂C≡CH | NH | N | 0 |
| CH₂C≡CH | NH | N | 1 |
| CH₂C≡CH | NH | N | 2 |
| CycPr | NH | N | 0 |
| CycPr | NH | N | 1 |
| CycPr | NH | N | 2 |
| CH₂CycPr | NH | N | 0 |
| CH₂CycPr | NH | N | 1 |
| CH₂CycPr | NH | N | 2 |

TABLE 9

| R¹ | A¹ | A² | n |
|---|---|---|---|
| Me | S | CH | 0 |
| Me | S | CH | 1 |
| Me | S | CH | 2 |
| Et | S | CH | 0 |
| Et | S | CH | 1 |
| Et | S | CH | 2 |
| Pr | S | CH | 0 |
| Pr | S | CH | 1 |
| Pr | S | CH | 2 |
| iPr | S | CH | 0 |
| iPr | S | CH | 1 |
| iPr | S | CH | 2 |
| tBu | S | CH | 0 |
| tBu | S | CH | 1 |
| tBu | S | CH | 2 |
| CF₃ | S | CH | 0 |
| CF₃ | S | CH | 1 |
| CF₃ | S | CH | 2 |
| CH₂CF₃ | S | CH | 0 |
| CH₂CF₃ | S | CH | 1 |
| CH₂CF₃ | S | CH | 2 |
| CH=CH₂ | S | CH | 0 |
| CH=CH₂ | S | CH | 1 |
| CH=CH₂ | S | CH | 2 |

TABLE 10

| R¹ | A¹ | A² | n |
|---|---|---|---|
| CH₂CH=CH₂ | S | CH | 0 |
| CH₂CH=CH₂ | S | CH | 1 |
| CH₂CH=CH₂ | S | CH | 2 |
| C≡CH | S | CH | 0 |
| C≡CH | S | CH | 1 |
| C≡CH | S | CH | 2 |
| CH₂C≡CH | S | CH | 0 |
| CH₂C≡CH | S | CH | 1 |
| CH₂C≡CH | S | CH | 2 |
| CycPr | S | CH | 0 |
| CycPr | S | CH | 1 |
| CycPr | S | CH | 2 |
| CH₂CycPr | S | CH | 0 |
| CH₂CycPr | S | CH | 1 |
| CH₂CycPr | S | CH | 2 |

TABLE 11

| R¹ | A¹ | A² | n |
|---|---|---|---|
| Me | S | N | 0 |
| Me | S | N | 1 |
| Me | S | N | 2 |
| Et | S | N | 0 |
| Et | S | N | 1 |
| Et | S | N | 2 |
| Pr | S | N | 0 |
| Pr | S | N | 1 |
| Pr | S | N | 2 |
| iPr | S | N | 0 |
| iPr | S | N | 1 |
| iPr | S | N | 2 |
| tBu | S | N | 0 |
| tBu | S | N | 1 |
| tBu | S | N | 2 |
| CF₃ | S | N | 0 |
| CF₃ | S | N | 1 |
| CF₃ | S | N | 2 |
| CH₂CF₃ | S | N | 0 |
| CH₂CF₃ | S | N | 1 |
| CH₂CF₃ | S | N | 2 |
| CH=CH₂ | S | N | 0 |
| CH=CH₂ | S | N | 1 |
| CH=CH₂ | S | N | 2 |

TABLE 12

| R¹ | A¹ | A² | n |
|---|---|---|---|
| CH₂CH=CH₂ | S | N | 0 |
| CH₂CH=CH₂ | S | N | 1 |
| CH₂CH=CH₂ | S | N | 2 |
| C≡CH | S | N | 0 |
| C≡CH | S | N | 1 |
| C≡CH | S | N | 2 |
| CH₂C≡CH | S | N | 0 |
| CH₂C≡CH | S | N | 1 |
| CH₂C≡CH | S | N | 2 |
| CycPr | S | N | 0 |
| CycPr | S | N | 1 |
| CycPr | S | N | 2 |
| CH₂CycPr | S | N | 0 |
| CH₂CycPr | S | N | 1 |
| CH₂CycPr | S | N | 2 |

TABLE 13

| R¹ | A¹ | A² | n |
|---|---|---|---|
| Me | O | CH | 0 |
| Me | O | CH | 1 |
| Me | O | CH | 2 |
| Et | O | CH | 0 |
| Et | O | CH | 1 |
| Et | O | CH | 2 |
| Pr | O | CH | 0 |
| Pr | O | CH | 1 |
| Pr | O | CH | 2 |
| iPr | O | CH | 0 |
| iPr | O | CH | 1 |
| iPr | O | CH | 2 |
| tBu | O | CH | 0 |
| tBu | O | CH | 1 |
| tBu | O | CH | 2 |
| CF₃ | O | CH | 0 |
| CF₃ | O | CH | 1 |
| CF₃ | O | CH | 2 |
| CH₂CF₃ | O | CH | 0 |
| CH₂CF₃ | O | CH | 1 |
| CH₂CF₃ | O | CH | 2 |
| CH=CH₂ | O | CH | 0 |
| CH=CH₂ | O | CH | 1 |
| CH=CH₂ | O | CH | 2 |

TABLE 14

| R¹ | A¹ | A² | n |
|---|---|---|---|
| CH₂CH=CH₂ | O | CH | 0 |
| CH₂CH=CH₂ | O | CH | 1 |
| CH₂CH=CH₂ | O | CH | 2 |
| C≡CH | O | CH | 0 |
| C≡CH | O | CH | 1 |
| C≡CH | O | CH | 2 |
| CH₂C≡CH | O | CH | 0 |
| CH₂C≡CH | O | CH | 1 |
| CH₂C≡CH | O | CH | 2 |
| CycPr | O | CH | 0 |
| CycPr | O | CH | 1 |
| CycPr | O | CH | 2 |
| CH₂CycPr | O | CH | 0 |
| CH₂CycPr | O | CH | 1 |
| CH₂CycPr | O | CH | 2 |

TABLE 15

| R¹ | A¹ | A² | n |
|---|---|---|---|
| Me | O | N | 0 |
| Me | O | N | 1 |
| Me | O | N | 2 |
| Et | O | N | 0 |
| Et | O | N | 1 |
| Et | O | N | 2 |
| Pr | O | N | 0 |
| Pr | O | N | 1 |
| Pr | O | N | 2 |
| iPr | O | N | 0 |
| iPr | O | N | 1 |
| iPr | O | N | 2 |
| tBu | O | N | 0 |
| tBu | O | N | 1 |
| tBu | O | N | 2 |
| CF₃ | O | N | 0 |
| CF₃ | O | N | 1 |
| CF₃ | O | N | 2 |
| CH₂CF₃ | O | N | 0 |
| CH₂CF₃ | O | N | 1 |
| CH₂CF₃ | O | N | 2 |
| CH=CH₂ | O | N | 0 |
| CH=CH₂ | O | N | 1 |
| CH=CH₂ | O | N | 2 |

TABLE 16

| R¹ | A¹ | A² | n |
|---|---|---|---|
| CH₂CH=CH₂ | O | N | 0 |
| CH₂CH=CH₂ | O | N | 1 |
| CH₂CH=CH₂ | O | N | 2 |
| C≡CH | O | N | 0 |
| C≡CH | O | N | 1 |
| C≡CH | O | N | 2 |
| CH₂C≡CH | O | N | 0 |
| CH₂C≡CH | O | N | 1 |
| CH₂C≡CH | O | N | 2 |
| CycPr | O | N | 0 |
| CycPr | O | N | 1 |
| CycPr | O | N | 2 |
| CH₂CycPr | O | N | 0 |
| CH₂CycPr | O | N | 1 |
| CH₂CycPr | O | N | 2 |

(In [Table 1] to [Table 16] above, Me represents a methyl group, Et represents an ethyl group, Pr represents an n-propyl group, iPr represents an isopropyl group, tBu represents a tert-butyl group, and CycPr represents a cyclopropyl group.)

In the formula (1), compounds wherein $R^2$ is a trifluoromethylsulfinyl group, $R^3$ is a trifluoromethyl group, and $R^1, A^1, A^2$ and n are the combinations shown in [Table 1] to [Table 16].

In the formula (1), compounds wherein $R^2$ is a trifluoromethylsulfonyl group, $R^3$ is a trifluoromethyl group, and $R^1, A^1, A^2$ and n are the combinations shown in [Table 1] to [Table 16].

In the formula (1), compounds wherein $R^2$ is a heptafluoroisopropyl group, $R^3$ is a trifluoromethyl group, and $R^1, A^1, A^2$ and n are the combinations shown in [Table 1] to [Table 16].

In the formula (1), compounds wherein $R^2$ is a trifluoromethylsulfanyl group, $R^3$ is a pentafluoroethyl group, and $R^1, A^1, A^2$ and n are the combinations shown in [Table 1] to [Table 16].

In the formula (1), compounds wherein $R^2$ is a trifluoromethylsulfinyl group, $R^3$ is a pentafluoroethyl group, and $R^1, A^1, A^2$ and n are the combinations shown in [Table 1] to [Table 16]

In the formula (1), compounds wherein $R^2$ is a trifluoromethylsulfonyl group, $R^3$ is a pentafluoroethyl group, and $R^1, A^1, A^2$ and n are the combinations shown in [Table 1] to [Table 16].

In the formula (1), compounds wherein $R^2$ is a heptafluoroisopropyl group, $R^3$ is a pentafluoroethyl group, and $R^1, A^1, A^2$ and n are the combinations shown in [Table 1] to [Table 16].

In the formula (1), compounds wherein $R^2$ is a trifluoromethylsulfanyl group, $R^3$ is a heptafluoroisopropyl group, and $R^1, A^1, A^2$ and n are the combinations shown in [Table 1] to [Table 16].

In the formula (1), compounds wherein $R^2$ is a trifluoromethylsulfinyl group, $R^3$ is a heptafluoroisopropyl group, and $R^1, A^1, A^2$ and n are the combinations shown in [Table 1] to [Table 16].

In the formula (1), compounds wherein $R^2$ is a trifluoromethylsulfonyl group, $R^3$ is a heptafluoroisopropyl group, and $R^1, A^1, A^2$ and n are the combinations shown in [Table 1] to [Table 16].

In the formula (1), compounds wherein $R^2$ is a heptafluoroisopropyl group, $R^3$ is a heptafluoroisopropyl group, and $R^1, A^1, A^2$ and n are the combinations shown in [Table 1] to [Table 16].

In the formula (1), compounds wherein $R^2$ is a trifluoromethylsulfanyl group, $R^3$ is a trifluoromethoxy group, and $R^1, A^1, A^2$ and n are the combinations shown in [Table 1] to [Table 16].

In the formula (1), compounds wherein $R^2$ is a trifluoromethylsulfinyl group, $R^3$ is a trifluoromethoxy group, and $R^1, A^1, A^2$ and n are the combinations shown in [Table 1] to [Table 16].

In the formula (1), compounds wherein $R^2$ is a trifluoromethylsulfonyl group, $R^3$ is a trifluoromethoxy group, and $R^1, A^1, A^2$ and n are the combinations shown in [Table 1] to [Table 16].

In the formula (1), compounds wherein $R^2$ is a heptafluoroisopropyl group, $R^3$ is a trifluoromethoxy group, and $R^1, A^1, A^2$ and n are the combinations shown in [Table 1] to [Table 16].

In the formula (1), compounds wherein $R^2$ is a trifluoromethylsulfanyl group, $R^3$ is a trifluoromethylsulfanyl group, and $R^1, A^1, A^2$ and n are the combinations shown in [Table 1] to [Table 16].

In the formula (1), compounds wherein $R^2$ is a trifluoromethylsulfinyl group, $R^3$ is a trifluoromethylsulfanyl group, and $R^1, A^1, A^2$ and n are the combinations shown in [Table 1] to [Table 16].

In the formula (1), compounds wherein $R^2$ is a trifluoromethylsulfonyl group, $R^3$ is a trifluoromethylsulfanyl group, and $R^1, A^1, A^2$ and n are the combinations shown in [Table 1] to [Table 16].

In the formula (1), compounds wherein $R^2$ is a heptafluoroisopropyl group, $R^3$ is a trifluoromethylsulfanyl group, and $R^1$, $A^1$, $A^2$ and n are the combinations shown in [Table 1] to [Table 16].
In the formula (1), compounds wherein $R^2$ is a trifluoromethylsulfanyl group, $R^3$ is a trifluoromethylsulfinyl group, and $R^1$, $A^1$, $A^2$ and n are the combinations shown in [Table 1] to [Table 16].
In the formula (1), compounds wherein $R^2$ is a trifluoromethylsulfinyl group, $R^3$ is a trifluoromethylsulfinyl group, and $R^1$, $A^1$, $A^2$ and n are the combinations shown in [Table 1] to [Table 16].
In the formula (1), compounds wherein $R^2$ is a trifluoromethylsulfonyl group, $R^3$ is a trifluoromethylsulfinyl group, and $R^1$, $A^1$, $A^2$ and n are the combinations shown in [Table 1] to [Table 16].
In the formula (1), compounds wherein $R^2$ is a heptafluoroisopropyl group, $R^3$ is a trifluoromethylsulfinyl group, and $R^1$, $A^1$, $A^2$ and n are the combinations shown in [Table 1] to [Table 16].
In the formula (1), compounds wherein $R^2$ is a trifluoromethylsulfanyl group, $R^3$ is a trifluoromethylsulfonyl group, and $R^1$, $A^1$, $A^2$ and n are the combinations shown in [Table 1] to [Table 16].
In the formula (1), compounds wherein $R^2$ is a trifluoromethylsulfinyl group, $R^3$ is a trifluoromethylsulfonyl group, and $R^1$, $A^1$, $A^2$ and n are the combinations shown in [Table 1] to [Table 16].
In the formula (1), compounds wherein $R^2$ is a trifluoromethylsulfonyl group, $R^3$ is a trifluoromethylsulfonyl group, and $R^1$, $A^1$, $A^2$ and n are the combinations shown in [Table 1] to [Table 16].
In the formula (1), compounds wherein $R^2$ is a heptafluoroisopropyl group, $R^3$ is a trifluoromethylsulfonyl group, and $R^1$, $A^1$, $A^2$ and n are the combinations shown in [Table 1] to [Table 16].

Examples of the pest on which the compound of the present invention has an effect include arthropod pests such as pest insects and pest mites and nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai*, *Homona magnanima*, *Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: *Culex* such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, *Stomoxys*, and Stomoxyidae.

Coleoptera: Corn rootworm such as *Diabrotica virgifera virgifera* and *Diabrotica undecimpunctata howardi*, Scarabaeidae such as *Anomala cuprea*, *Anomala rufocuprea*, and *Popillia japonica*, Curculionidae such as *Sitophilus zeamais*, *Lissorhoptrus oryzophilus*, *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, *Epilachna* such as *Epilachna vigintioctopunctata*, Lyctidae such as *Lyctus brunneus* and *Tomicus piniperda*, Bostrychidae, Ptinidae, Cerambycidae such as *Anoplophora malasiaca*, *Agriotes* spp., and *Paederus fuscipes*.

Orthoptera: *Locusta migratoria*, *Gryllotalpa africana*, *Oxya yezoensis*, *Oxya japonica*, and Grylloidea.

Siphonaptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophaga: *Dalmalinia ovis*, *Dalmalinia bovis*, *Menopon gallinae*, *Trichodectes canis*, *Felicola subrostrata*, and the like.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, and *Pratylenchus neglectus*.

Blattodea: *Blattella germanica*, *Periplaneta fuliginosa*, *Periplaneta americana*, *Periplaneta brunnea*, and *Blatta orientalis*.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, and the like.

Acarina: Tetranychidae such as *Tetranychus urticae, Tetranychus kanzawai, Panonychus citri, Panonychus ulmi,* and *Oligonychus* spp., Eriophyidae such as *Aculops pelekassi, Phyllocoptruta citri, Aculops lycopersici, Calacarus carinatus, Acaphylla theavagrans, Eriophyes chibaensis,* and *Aculus schlechtendali,* Tarsonemidae such as *Polyphagotarsonemus latus,* Tenuipalpidae such as *Brevipalpus phoenicis,* Tuckerellidae, Metastigmata such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus,* and *Rhipicephalus sanguineus,* Acaridae such as *Tyrophagus putrescentiae* and *Tyrophagus similis,* Pyroglyphidae such as *Dermatophagoides farinae* and *Dermatophagoides ptrenyssnus,* Cheyletidae such as *Cheyletus eruditus, Cheyletus malaccensis, Cheyletus moorei,* and *Cheyletiella yasguri,* Sarcoptidae such as *Octodectes cynotis* and *Sacroptes scabiei,* Demodicidae such as *Demodex canis,* Listrophoridae, Oribatei, Dermanyssidae such as *Ornithonyssus bacoti, Ornithonyssus sylvairum,* and *Dermanyssus gallinae,* Trombiculidae such as *Leptotrombidium akamushi,* Arachnida such as *Chiracanthium japonicum* and *Latrodectus hasseltii,* and the like.

Chilopoda: *Thereuonema hilgendorfi, Scolopendra subspinipes,* and the like.

Diplopoda: *Oxidus gracilis, Nedyopus tambanus,* and the like.

Isopoda: *Armadillidium vulgare,* and the like.

Gastropoda: *Limax marginatus, Limax flavus,* and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, smoking agents, poisonous baits, resin formulations, shampoo agents, paste formulations, foam agents, carbon dioxide preparations, tablets, and the like. These formulations may be processed into mosquito repellent coils, electric mosquito repellent mats, mosquito repellent liquid formulations, smoking agents, fumigants, sheet formulations, spot-on agents, or oral treatment agents, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like, and synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, and then molding it by injection molding, extrusion molding, press molding or the like, and can be processed into a plate, film, taped, reticular or string resin formulation by further undergoing molding or cutting step as necessary. These resin formulation is processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant such as cheese flavor, onion flavor and peanut oil or the like are added as necessary.

The method for controlling pests of the present invention is carried out by applying an effective amount of the compound of the present invention to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g per the amount of the compound of the present invention per 10000 m². When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on a pest or a plant such as crops which should be protected from pests, and also may be applied on a soil in order to control a pest that infests in the soil of cultivated land.

Also, the resin formulation processed into a sheet or string can be also applied by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 m$^2$ of an area to be treated, in the case of using it on a planar area, and is usually 0.01 to 500 mg in an amount of the compound of the present invention per 1 m$^3$ of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, smoking agents, poisonous baits and the like are applied as they are. When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention when administered to an animal body is usually in the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland *chrysanthemum*, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (*Satsuma* mandarin, orange, lemon, lime, grapefruits, etc.), nuts (chestnut, walnut, hazel nut, almond, pistachio, cashew nut, *macadamia* nut, etc.), berry fruits (blueberry, cranberry, blackberry, raspberry, etc.), grape, *persimmon*, olive, loquat, banana, coffee, date, coconut, oil palm, etc.

Trees other than fruit trees: tea, mulberry, flowering trees and shrubs (azalea, *camellia, hydrangea, sasanqua, Illicium religiosum*, cherry tree, tulip tree, crape myrtle, fragrant olive, etc.), street trees (ash tree, birch, dogwood, *eucalyptus,* *ginkgo*, lilac, maple tree, oak, poplar, *cercis*, Chinese sweet gum, plane tree, *zelkova*, Japanese arborvitae, fir tree, Japanese hemlock, needle juniper, pine, spruce, yew, elm, horse-chestnut, etc.), sweet *viburnum, Podocarpus macrophyllus*, Japanese cedar, Japanese cypress, *croton*, spindle tree, Chainese howthorn, etc.

Lawn: *zoysia* (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, *chrysanthemum, Eustoma grandiflorum* Shinners (prairie gentian), *gypsophila, gerbera*, pot marigold, *salvia, petunia, verbena*, tulip, *aster*, gentian, lily, pansy, *cyclamen*, orchid, lily of the valley, lavender, stock, ornamental kale, *primula*, poinsttia, *gladiolus, cattleya*, daisy, *cymbidium, begonia*, etc.), bio-fuel plants (*Jatropha, curcas*, safflower, *Camelina alyssum*, switchgrass, *miscanthus*, reed canary grass, *Arundo donax*, kenaf, cassava, willow, algae, etc.), foliage plants, etc.

The "crops" also contains genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl(EZ)-(1RS,3RS;1RS, 3SR)-2,2-dimethyl-3-prop-1-enylcyclopropanecarboxylate, 2,3,5,6-tetrafluoro-4-methylbenzyl(EZ)-(1RS, 3RS; 1RS, 3SR)-2,2-dimethyl-3-prop-1-enylcyclopropanecarboxylate, and 2,3,5,6-tetrafluoro-4-(methoxymethyl)benzyl(1RS, 3RS; 1RS,3SR)-2,2-dimethyl-3-(2-methyl-1-propenyl)cyclopropanecarboxylate, 2,3,5,6-tetrafluoro-4-(methoxymethyl)benzyl(EZ)-(1RS,3RS; 1RS,3SR)-2,2-dimethyl-3-(2-cyano-1-propenyl)cyclopropanecarboxylate.

(4) Nereistoxin Compounds cartap, bensultap, thiocyclam, monosultap, andbisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof.

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, compounds represented by the following formula (K):

(K)

wherein $R^{100}$ represents chlorine, bromine or a trifluoromethyl group, $R^{200}$ represents chlorine, bromine or a methyl group, and $R^{300}$ represents chlorine, bromine or a cyano group, and compounds represented by the following formula (L):

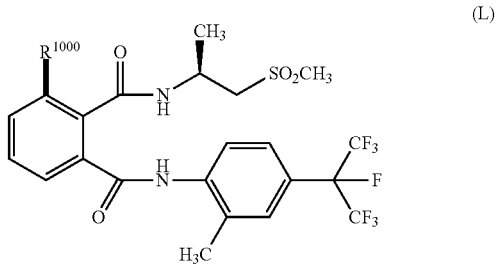

wherein $R^{1000}$ represents chlorine, bromine or iodine.

Active Ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active Ingredients of Fungicide azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol; Cyclic amine fungicidal compounds such as fenpropimorph, tridemorph, and fenpropidin; Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Herbicide (1) Phenoxy Fatty Acid Herbicidal Compounds 2,4-PA, MCP, MCPB, phenothiol, mecoprop, fluroxypyr, triclopyr, clomeprop, and naproanilide.

(2) Benzoate Herbicidal Compounds 2,3,6-TBA, dicamba, clopyralid, picloram, aminopyralid, quinclorac, and quinmerac.

(3) Urea Herbicidal Compounds diuron, linuron, chlortoluron, isoproturon, fluometuron, isouron, tebuthiuron, methabenzthiazuron, cumyluron, daimuron, and methyl-daimuron.

(4) Triazine Herbicidal Compounds atrazine, ametoryn, cyanazine, simazine, propazine, simetryn, dimethametryn, prometryn, metribuzin, triaziflam, and indaziflam.

(5) Bipyridinium Herbicidal Compounds paraquat, and diquat.

(6) Hydroxybenzonitrile Herbicidal Compounds
bromoxynil, and ioxynil.
(7) Dinitroaniline Herbicidal Compounds
pendimethalin, prodiamine, and trifluralin.
(8) Organophosphorus Herbicidal Compounds
amiprofos-methyl, butamifos, bensulide, piperophos, anilofos, glyphosate, glufosinate, glufosinate-P, and bialaphos.
(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds
propanil, propyzamide, bromobutide, and etobenzanid.
(11) Chloroacetanilide Herbicidal Compounds
acetochlor, alachlor, butachlor, dimethenamid, propachlor, metazachlor, metolachlor, pretilachlor, thenylchlor, and pethoxamid.
(12) Diphenyl Ether Herbicidal Compounds
acifluorfen-sodium, bifenox, oxyfluorfen, lactofen, fomesafen, chlomethoxynil, and aclonifen.
(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds
benzofenap, pyrazolate, pyrazoxyfen, topramezone, and pyrasulfotole.
(15) Triketone Herbicidal Compounds
isoxaflutole, benzobicyclon, sulcotrione, mesotrione, tembotrione, and tefuryltrione.
(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
chlorsulfuron, sulfometuron-methyl, metsulfuron-methyl, chlorimuron-ethyl, tribenuron-methyl, triasulfuron, metsulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
imazamethabenz-methyl, imazamethapyr, imazamox, imazapyr, imazaquin, and imazethapyr.
(20) Sulfonamide Herbicidal Compounds
flumetsulam, metosulam, diclosulam, florasulam, cloransulam-methyl, penoxsulam, and pyroxsulam.
(21) Pyrimidinyloxybenzoate Herbicidal Compounds
pyrithiobac-sodium, bispyribac-sodium, pyriminobac-methyl, pyribenzoxim, pyriftalid, and pyrimisulfan.
(22) Other Herbicidal Compounds bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Plant Growth Regulator hymexazol, paclobutrazol, uniconazole-P, inabenfide, prohexadione-calcium, aviglycine, 1-naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride and 4-CPA (4-chlorophenoxyacetic acid).

Active Ingredients of Synergist piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, CH3I, t-phenylbutenone, diethylmaleate, DMC, FDMC, ETP, and ETN.

EXAMPLES

Hereinbelow, the present invention will be further described in detail by production examples, formulation examples, test examples, and the like. However, the present invention is not limited to these examples.

First, the production examples for the production of the compounds of the present invention are shown below.

Production Example 1 (1)

0.21 g of sodium ethanethiolate (80%) was added to a mixture of 0.55 g of 1-bromo-2-fluoro-4-trifluoromethylsulfanylbenzene and 4 ml of THF under ice cooling, and the mixture was stirred at room temperature for 30 minutes. 2 mL of DMF was added to the reaction mixture, and the mixture was stirred at 80° C. for 2 hours. A saturated aqueous sodium bicarbonate solution was added to the cooled reaction mixture, and the mixture was extracted with ethyl acetate and then dried with anhydrous sodium sulfate. The mixture was concentrated under reduced pressure, and the resulting residue was applied to a silica gel column chromatography to obtain 0.37 g of 1-bromo-2-ethylsulfanyl-4-trifluoromethylsulfanylbenzene.

1-Bromo-2-ethylsulfanyl-4-trifluoromethylsulfanyl-benzene

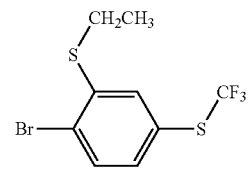 [SMILES: CCSc1cc(SC(F)(F)F)ccc1Br]

1H-NMR (CDCl$_3$) δ: 7.58 (1H, d), 7.41 (1H, d), 7.26 (1H, dd), 2.99 (2H, q), 1.41 (3H, t).

Production Example 1 (2)

A mixture of 23.9 g of 2-chloro-5-iodopyridine, 14 ml of thiobenzoic acid, 1.90 g of copper iodide, 3.60 g of 1,10-phenanthroline, 35 ml of diisopropylethylamine and 200 ml of toluene was stirred at 110° C. for 4 hours. Water was added to the reaction mixture cooled to room temperature, and the insoluble matter was filtered with celite (registered trademark), and then the filtered matter was washed with ethyl acetate, and the filtrate was extracted with ethyl acetate. The combined organic layer was dried over anhydrous magnesium sulfate and then concentrated under reduced pressure. The resulting residue was applied to a silica gel column chromatography to obtain 21.2 g of thiobenzoic acid S-(6-chloropyridin-3-yl)ester.

Thiobenzoic acid S-(6-chloropyridin-3-yl)ester

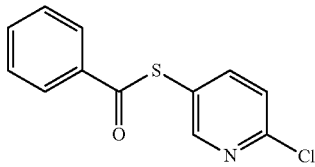 [SMILES: O=C(Sc1ccc(Cl)nc1)c1ccccc1]

$^1$H-NMR (CDCl$_3$) δ: 8.43-8.42 (1H, m), 8.01-7.98 (2H, m), 7.79-7.76 (1H, m), 7.66-7.61 (1H, m), 7.52-7.47 (2H, m), 7.44-7.41 (1H, m).

Production Example 1 (3)

A mixture of 21.2 g of thiobenzoic acid S-(6-chloropyridin-3-yl)ester, 17.6 g of potassium carbonate and 170 ml of methanol was stirred at room temperature for 2 hours. The reaction mixture was filtered, and the filtered matter was washed with methanol, and then the filtrate was concentrated under reduced pressure. 170 ml of a 1 N aqueous sodium hydroxide solution was added to the resulting crude product, an aqueous solution of 56.0 g of potassium ferricyanide was added dropwise, and the mixture was stirred at room temperature for 2 hours. The reaction mixture was extracted with methyl-tert-butyl ester. The combined organic layer was dried over anhydrous magnesium sulfate and then concentrated under reduced pressure. The residue was applied to a silica gel column chromatography to obtain 11.5 g of a compound represented by
the following formula:

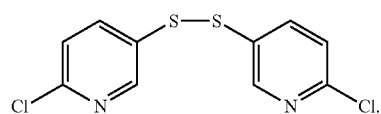 [SMILES: Clc1ccc(SSc2ccc(Cl)nc2)cn1]

$^1$H-NMR (CDCl$_3$) δ: 8.41 (2H, d), 7.74 (2H, dd), 7.29 (2H, d).

Production Example 1 (4)

A mixture of 11.5 g of a compound represented by the following formula:

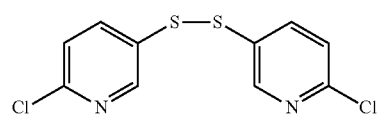

and 133 ml of DMF was cooled to −50° C., and an excess amount of CF$_3$I gas was bubbled to dissolve the compound in DMF. 37.0 ml of tetrakisdimethylaminoethylenediamine was added dropwise at a rate such that the internal temperature does not surpass −40° C. Thereafter, the mixture was heated to −10° C. over 1 hour and further stirred at −10° C. for 2 hours. Water was added to the reaction mixture, and the mixture was heated to room temperature and then extracted with ethyl acetate. The combined organic layer was dried over anhydrous magnesium sulfate and then concentrated under reduced pressure. The resulting residue was applied to a silica gel column chromatography to obtain 7.25 g of 2-chloro-5-trifluoromethylsulfanylpyridine.

2-Chloro-5-trifluoromethylsulfanylpyridine

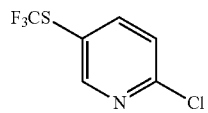

$^1$H-NMR (CDCl$_3$) δ: 8.62 (1H, d), 7.93 (1H, dd), 7.43 (1H, d).

Production Example 1 (5)

1.86 g of an aqueous methylamine solution (40%) was added dropwise to a mixture of 1.71 g of 2-chloro-5-trifluoromethylsulfanylpyridine and 16 ml of NMP, and then the mixture was heated to 60° C. and heated and stirred for 2 hours. After cooling the mixture to room temperature, 1.66 g of potassium carbonate was added, and 1.86 g of a 40% aqueous methylamine solution was added dropwise. The mixture was heated to 60° C. and further heated and stirred for 2 hours. After cooling the mixture to room temperature, water was added, and the mixture was extracted with ethyl acetate. The combined organic layer was dried over anhydrous magnesium sulfate and then concentrated under reduced pressure. The resulting residue was applied to a silica gel column chromatography to obtain 1.52 g of methyl-(5-trifluoromethylsulfanylpyridin-2-yl)-amine.

Methyl-(5-trifluoromethylsulfanylpyridin-2-yl)-amine

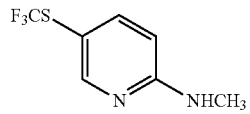

$^1$H-NMR (CDCl$_3$) δ: 8.28 (1H, d), 7.63 (1H, dd), 6.41-6.38 (1H, m), 4.90 (1H, brs), 2.96 (3H, d,).

Production Example 1 (6)

1.43 g of N-bromosuccinimide was added to a mixture of 1.52 g of methyl-(5-trifluoromethylsulfanylpyridin-2-yl)-amine and 24 ml of chloroform, and the mixture was stirred at room temperature for 1 hour. Water was added to the reaction mixture, and the mixture was extracted with chloroform. The combined organic layer was dried over anhydrous sodium sulfate and then concentrated under reduced pressure. The resulting residue was applied to a silica gel column chromatography to obtain 1.96 g of (3-bromo-5-trifluoromethylsulfanylpyridin-2-yl)-methylamine.

(3-Bromo-5-trifluoromethylsulfanylpyridin-2-yl)-methylamine

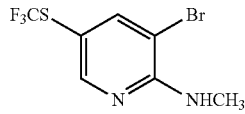

$^1$H-NMR (CDCl$_3$) δ: 8.28 (1H, d), 7.83 (1H, d), 5.40 (1H, brs), 3.07 (3H, d).

Production Example 1 (7)

1.96 g of (3-bromo-5-trifluoromethylsulfanylpyridin-2-yl)-methylamine, 89 mg of acetylacetone copper(II), 0.27 g of acetylacetone, 2.34 g of cesium carbonate, 7 ml of NMP and 5 ml of aqueous ammonia (28%) were charged to a pressure-resistant reactor and stirred at 110° C. for 8.5 hours. Water was added to the reaction mixture cooled to room temperature, and the insoluble matter was filtered with celite (registered trademark), and then the filtered matter was washed with ethyl acetate, and the filtrate was extracted with ethyl acetate. The combined organic layer was dried over anhydrous sodium sulfate and then concentrated under reduced pressure. The resulting residue was applied to a silica gel column chromatography to obtain 1.18 g of N$^2$-methyl-5-trifluoromethylsulfanylpyridine-2,3-diamine.

N$^2$-Methyl-5-trifluoromethylsulfanylpyridine-2,3-diamine

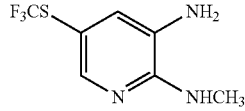

$^1$H-NMR (CDCl$_3$) δ: 8.01-7.99 (1H, m), 7.07-7.05 (1H, m), 4.60 (1H, brs), 3.22 (2H, brs), 3.05 (3H, d).

Production Example 1 (8)

A mixture of 10.0 g of N$^2$-methyl-5-trifluoromethylsulfanylpyridine-2,3-diamine, 41 ml of formic acid and 5 ml of water was stirred under heating and refluxing for 2 hours. The reaction mixture was concentrated under reduced pressure, a saturated aqueous sodium bicarbonate solution was added to the resulting residue, and the mixture was extracted with methyl-tert-butyl ether. The organic layer was dried over anhydrous magnesium sulfate and then concentrated under reduced pressure. The residue was applied to a silica gel column chromatography to obtain 7.80 g of 3-methyl-6-trifluoromethylsulfanyl-3H-imidazo[4,5-b]pyridine.

3-Methyl-6-trifluoromethylsulfanyl-3H-imidazo[4,5-b]pyridine

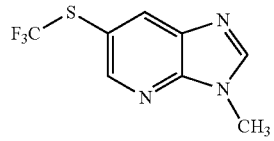

$^1$H-NMR (CDCl$_3$) δ: 8.65 (1H, d), 8.39 (1H, d), 8.14 (1H, s), 3.96 (3H, s).

Production Example 1 (9)

A mixture of 0.11 g of 3-methyl-6-trifluoromethylsulfanyl-3H-imidazo[4,5-b]pyridine, 0.15 g of 1-bromo-2-ethylsulfanyl-4-trifluoromethylsulfanylbenzene, 0.01 g of palladium(II) acetate, 0.01 g of triphenylphosphine, 0.02 g of copper(II) acetate monohydrate, 0.13 g of potassium carbonate and 3 ml of toluene was stirred under heating and refluxing for 2 hours. Ethyl acetate and water were added to the cooled reaction mixture, and the mixture was filtered. The filtrate was extracted with ethyl acetate, and then dried over anhydrous sodium sulfate. The mixture was concentrated under reduced pressure, and the resulting residue was applied to a silica gel column chromatography to obtain 0.20 g of 2-(2-ethylsulfanyl-4-trifluoromethylsulfanylphenyl)3-methyl-6-trifluoromethylsulfanyl-3H-imidazo[4,5-b]pyridine (hereinafter, referred to as Compound 7).

Compound 7

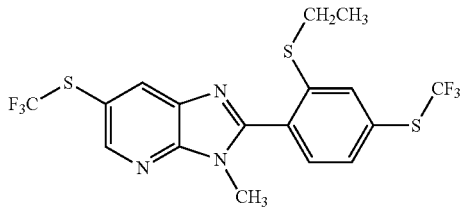

$^1$H-NMR (CDCl$_3$) δ: 8.68 (1H, s), 8.41 (1H, s), 7.71 (1H, s), 7.61 (1H, d), 7.49 (1H, d), 3.78 (3H, s), 2.95 (2H, q), 1.29 (3H, t).

Production Example 2 (1)

28 g of sodium pentafluoropropionate and 14 g of copper iodide were added to a mixture of 7.2 g of 2-chloro-5-iodopyridine, 75 ml of NMP and 75 ml of xylene under room temperature, and the mixture was heated to 150° C. and heated and stirred for 5.5 hours. After cooling the mixture to 80° C., 180 ml of an aqueous methylamine solution (40%) was added in 4 parts every 2 hours, and the mixture was heated and stirred for 8.5 hours. After the reaction, the mixture was ice-cooled to 0° C, a 28% aqueous ammonia solution and a saturated aqueous sodium bicarbonate solution were added, and the mixture was extracted with methyl tert-butyl ether (hereinafter, referred to as MTBE). The combined organic layer was dried over anhydrous sodium sulfate and then concentrated under reduced pressure. The residue was applied to a silica gel column chromatography to obtain 4.6 g of methyl-(5-pentafluoroethyl-pyridin-2-yl)-amine.

Methyl-(5-pentafluoroethyl-pyridin-2-yl)-amine

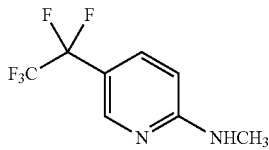

¹H-NMR (CDCl₃) δ: 8.28 (1H, d), 7.56 (1H, dd), 6.41 (1H, d), 5.74 (1H, brs), 2.95 (3H, d).

Production Example 2 (2)

5.0 g of N-bromosuccinimide was added to a mixture of 4.6 g of methyl-(5-pentafluoroethyl-pyridin-2-yl)-amine and 70 ml of acetonitrile, and the mixture was stirred at room temperature for 8 hours. A saturated aqueous sodium thiosulfate solution and an aqueous sodium bicarbonate solution were added to the mixture, and the mixture was extracted with ethyl acetate. The combined organic layer was dried over sodium sulfate and then concentrated under reduced pressure. The residue was applied to a silica gel column chromatography to obtain 6.3 g of (3-bromo-5-pentafluoroethyl-pyridin-2-yl)-methyl-amine.

(3-Bromo-5-pentafluoroethyl-pyridin-2-yl)-methyl-amine

¹H-NMR (CDCl₃) δ: 8.29 (1H, d), 7.74 (1H, d), 5.45 (1H, brs), 3.09 (3H, d).

Production Example 2 (3)

2.0 g of (3-bromo-5-pentafluoroethyl-pyridin-2-yl)-methyl-amine, 86 mg of acetylacetone copper(II), 263 mg of acetylacetone, 3.2 g of cesium carbonate and 13 ml of NMP were charged to an autoclave reactor, and 5 ml of an aqueous ammonia solution (28%) was added under ice cooling. After sealing the reactor, the mixture was heated to 110° C. and heated and stirred for 15 hours. After ice-cooling the mixture to room temperature, the reaction mixture was diluted with water and extracted with MTBE. The combined organic layer was dried over anhydrous sodium sulfate and then concentrated under reduced pressure. The residue was applied to a silica gel column chromatography to obtain 623 mg of N²-methyl-5-pentafluoroethyl-2,3-diamine.

N²-Methyl-5-pentafluoroethyl-2,3-diamine

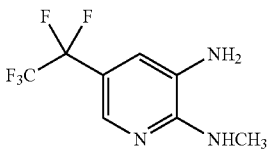

¹H-NMR (CDCl₃) δ: 7.99 (1H, d), 6.94 (1H, d), 4.64 (1H, brs), 3.30 (2H, brs), 3.06 (3H, d).

Production Example 2 (4)

A mixture of 0.42 g of N²-methyl-5-pentafluoroethylpyridine-2,3-diamine, 4 ml of formic acid and 0.5 ml of water was stirred under heating and refluxing for 2 hours. A saturated aqueous sodium bicarbonate solution was added to the reaction mixture, and the mixture was extracted with ethyl acetate. The organic layer was dried over anhydrous sodium sulfate and then concentrated under reduced pressure. The residue was applied to a silica gel column chromatography to obtain 7.80 g of 3-methyl-6-pentafluoroethyl-3H-imidazo[4,5-b]pyridine.

3-Methyl-6-pentafluoroethyl-3H-imidazo[4,5-b]pyridine

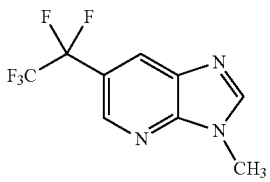

¹H-NMR (CDCl₃) δ: 8.65 (1H, s), 8.30 (1H, s), 8.18 (1H, s), 3.98 (3H, s).

Production Example 2 (5)

A mixture of 0.12 g of 3-methyl-6-pentafluoroethyl-3H-imidazo[4,5-b]pyridine, 0.15 g of 1-bromo-2-ethylsulfanyl-4-trifluoromethylsulfanylbenzene, 0.01 g of palladium(II) acetate, 0.01 g of triphenylphosphine, 0.02 g of copper(II) acetate monohydrate, 0.13 g of potassium carbonate and 3 ml of toluene was stirred under heating and refluxing for 2 hours. Ethyl acetate and water were added to the cooled reaction mixture, and the mixture was filtered. The filtrate was extracted with ethyl acetate, and then dried over anhydrous sodium sulfate. The mixture was concentrated under reduced pressure, and the resulting residue was applied to a silica gel column chromatography to obtain 0.19 g of 2-(2-ethylsulfanyl-4-trifluoromethylsulfanylphenyl)3-methyl-6-pentafluoroethyl-3H-imidazo[4,5-b]pyridine (hereinafter, referred to as Compound 8).

Compound 8

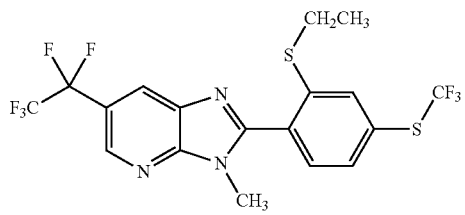

¹H-NMR (CDCl₃) δ: 8.68 (1H, d), 8.31 (1H, d), 7.71 (1H, d), 7.62 (1H, dd), 7.49 (1H, d), 3.80 (3H, s), 2.95 (2H, q), 1.29 (3H, t).

Production Example 3

0.20 g of 3-chloroperoxybenzoic acid (purity of 65% or more) was added to a mixture of 0.20 g of 2-(2-ethylsulfanyl-4-trifluoromethylsulfanylphenyl)3-methyl-6-trifluoromethylsulfanyl-3H-imidazo[4,5-b]pyridine and 3 ml of chloroform under ice cooling, and then the mixture was stirred under ice cooling for 2 hours. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and then concentrated under reduced pressure. The resulting residue was applied to a silica gel column chromatography to obtain 0.22 g of 2-(2-ethylsulfonyl-4-trifluoromethylsulfanylphenyl)3-methyl-6-trifluoromethylsulfanyl-3H-imidazo[4,5-b]pyridine (hereinafter, referred to as Compound 9).

Compound 9

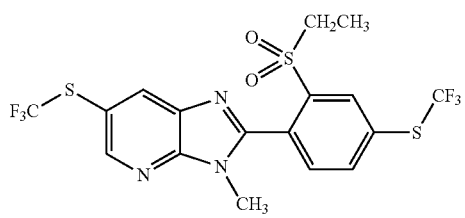

¹H-NMR (CDCl₃) δ: 8.70 (1H, d), 8.49 (1H, d), 8.36 (1H, d), 8.11 (1H, d), 7.63 (1H, d), 3.73 (3H, s), 3.47 (2H, q), 1.28 (3H, t).

Production Example 4

0.19 g of 3-chloroperoxybenzoic acid (purity of 65% or more) was added to a mixture of 0.19 g of 2-(2-ethylsulfanyl-4-trifluoromethylsulfanylphenyl)3-methyl-6-pentafluoroethyl-3H-imidazo[4,5-b]pyridine and 3 ml of chloroform under ice cooling, and then the mixture was stirred under ice cooling for 2 hours. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and then concentrated under reduced pressure. The resulting residue was applied to a silica gel column chromatography to obtain 0.22 g of 2-(2-ethylsulfonyl-4-trifluoromethylsulfanylphenyl)3-methyl-6-pentafluoroethyl-3H-imidazo[4,5-b]pyridine (hereinafter, referred to as Compound 10).

Compound 10

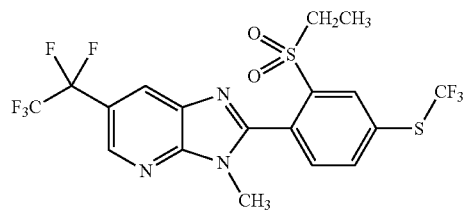

¹H-NMR (CDCl₃) δ: 8.71 (1H, s), 8.49 (1H, s), 8.27 (1H, s), 8.11 (1H, d), 7.63 (1H, d), 3.75 (3H, s), 3.47 (2H, q), 1.28 (3H, t).

Production Example 5 (1)

A mixture of 0.50 g of 2-amino-4-trifluoromethylsulfanylphenol and 3 ml of triethyl orthoformate was stirred under heating and refluxing for 3 hours. A saturated aqueous sodium bicarbonate solution was added to the reaction mixture, and the mixture was extracted with ethyl acetate. The organic layer was dried over anhydrous sodium sulfate and then concentrated under reduced pressure. The residue was applied to a silica gel column chromatography to obtain 0.50 g of 5-trifluoromethylsulfanylbenzoxazole.

5-Trifluoromethylsulfanylbenzoxazole

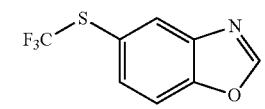 [SMILES: FC(F)(F)Sc1ccc2ocnc2c1]

¹H-NMR (CDCl₃) δ: 8.18 (1H, s), 8.15 (1H, d), 7.72 (1H, dd), 7.66 (1H, d).

Production Example 5 (2)

0.71 g of 3-chloroperoxybenzoic acid (purity of 65% or more) was added to a mixture of 0.50 g of 5-trifluoromethylsulfanylbenzoxazole and 3 ml of chloroform under ice cooling, and then the mixture was stirred at room temperature for 1 day. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and then concentrated under reduced pressure. The resulting residue was applied to a silica gel column chromatography to obtain 0.20 g of 5-trifluoromethylsulfinylbenzoxazole.

5-Trifluoromethylsulfinylbenzoxazole

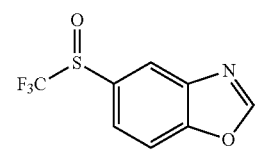 [SMILES: O=S(c1ccc2ocnc2c1)C(F)(F)F]

$^1$H-NMR (DMSO-D$_6$) δ: 9.03 (1H, s), 8.41 (1H, dd), 8.18 (1H, dd), 7.99 (1H, dd).

Production Example 5 (3)

A mixture of 0.10 g of 5-trifluoromethylsulfinylbenzoxazole, 0.15 g of 1-bromo-2-ethylsulfanyl-4-trifluoromethylsulfanylbenzene, 0.01 g of palladium(II) acetate, 0.01 g of triphenylphosphine, 0.02 g of copper(II) acetate monohydrate, 0.13 g of potassium carbonate and 3 ml of toluene was stirred under heating and refluxing for 2 hours. Ethyl acetate and water were added to the cooled reaction mixture, and the mixture was extracted with ethyl acetate and then dried with anhydrous sodium sulfate. The residue obtained by concentrating the mixture under reduced pressure was applied to a silica gel column chromatography to obtain 0.03 g of 2-(2-ethylsulfanyl-4-trifluoromethylsulfanyl-phenyl)-5-trifluoromethylsulfanylbenzoxazole (hereinafter, referred to as Compound 19).

Compound 19

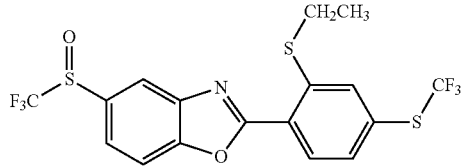

$^1$H-NMR (CDCl$_3$) δ: 8.34 (1H, s), 8.25 (1H, d), 7.91-7.84 (2H, m), 7.66 (1H, s), 7.55 (1H, dd), 3.11 (2H, q), 1.48 (3H, t).

The compounds described in the production examples described above and the compounds produced according to the method described in the production examples described above are shown in Table 17.
Compounds Represented by Formula (1).

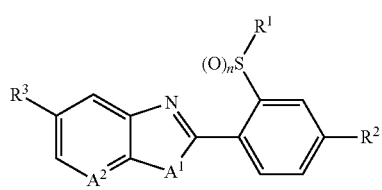

R$^1$, R$^2$, R$^3$, A$^1$, A$^2$ and n in the formula (1) represent the combinations shown in [Table 17] shown below.

TABLE 17

| Compound | R$^1$ | R$^2$ | R$^3$ | A$^1$ | A$^2$ | n |
|---|---|---|---|---|---|---|
| 1 | CH$_2$CH$_3$ | SCF$_3$ | CF$^3$ | NCH$_3$ | N | 2 |
| 2 | CH$_2$CH$_3$ | SO$_2$CF$_3$ | CF$^3$ | NCH$_3$ | N | 2 |
| 3 | CH$_2$CH$_3$ | SOCF$_3$ | CF$^3$ | NCH$_3$ | N | 2 |
| 4 | CH$_2$CH$_3$ | CF(CF$_3$)$_2$ | CF$^3$ | NCH$_3$ | N | 0 |
| 5 | CH$_2$CH$_3$ | CF(CF$_3$)$_2$ | CF$^3$ | NCH$_3$ | N | 1 |
| 6 | CH$_2$CH$_3$ | CF(CF$_3$)$_2$ | CF$^3$ | NCH$_3$ | N | 2 |
| 7 | CH$_2$CH$_3$ | SCF$_3$ | SCF$_3$ | NCH$_3$ | N | 0 |
| 8 | CH$_2$CH$_3$ | SCF$_3$ | CF$_2$CF$_3$ | NCH$_3$ | N | 0 |
| 9 | CH$_2$CH$_3$ | SCF$_3$ | SCF$_3$ | NCH$_3$ | N | 2 |
| 10 | CH$_2$CH$_3$ | SCF$_3$ | CF$_2$CF$_3$ | NCH$_3$ | N | 2 |
| 11 | CH$_2$CH$_3$ | SCF$_3$ | CF$_3$ | O | N | 0 |
| 12 | CH$_2$CH$_3$ | SCF$_3$ | SCF$_3$ | O | N | 0 |
| 13 | CH$_2$CH$_3$ | SCF$_3$ | SOCF$_3$ | O | N | 0 |

TABLE 17-continued

| Compound | R$^1$ | R$^2$ | R$^3$ | A$^1$ | A$^2$ | n |
|---|---|---|---|---|---|---|
| 14 | CH$_2$CH$_3$ | SCF$_3$ | SO$_2$CF$_3$ | O | N | 0 |
| 15 | CH$_2$CH$_3$ | SCF$_3$ | CF$_2$CF$_3$ | O | N | 0 |
| 16 | CH$_2$CH$_3$ | SCF$_3$ | CF$_3$ | O | CH | 0 |
| 17 | CH$_2$CH$_3$ | SCF$_3$ | SCF$_3$ | O | CH | 0 |
| 18 | CH$_2$CH$_3$ | SCF$_3$ | CF$_2$CF$_3$ | O | CH | 0 |
| 19 | CH$_2$CH$_3$ | SCF$_3$ | SOCF$_3$ | O | CH | 0 |
| 20 | CH$_2$CH$_3$ | SCF$_3$ | SO$_2$CF$_3$ | O | CH | 0 |

$^1$H-NMR data of the compounds shown in [Table 17] are shown below.
Compound 1
 $^1$H-NMR (CDCl$_3$) δ: 8.77-8.76 (1H, m), 8.50-8.49 (1H, m), 8.30-8.29 (1H, m), 8.13-8.10 (1H, m), 7.64 (1H, d), 3.75 (3H, s), 3.46 (2H, q), 1.28 (3H, t)
Compound 2
 $^1$H-NMR (CDCl$_3$) δ: 8.87-8.85 (1H, m), 8.80-8.79 (1H, m), 8.51-8.48 (1H, m), 8.33-8.32 (1H, m), 7.91 (1H, d), 3.78 (3H, s), 3.53 (2H, q), 1.30 (3H, t)
Compound 3
 $^1$H-NMR (CDCl$_3$) δ: 8.77-8.75 (1H, m), 8.56-8.54 (1H, m), 8.33-8.28 (2H, m), 7.84 (1H, d), 3.74 (3H, s), 3.52-3.44 (2H, m), 1.25 (3H, t)
Compound 4
 $^1$H-NMR (CDCl$_3$) δ: 8.75-8.74 (1H, m), 8.35-8.33 (1H, m), 7.69-7.67 (1H, m), 7.59-7.58 (2H, m), 3.82 (3H, s), 2.93 (2H, q), 1.27 (3H, t)
Compound 5
 $^1$H-NMR (CDCl$_3$) δ: 8.80-8.78 (1H, m), 8.55-8.53 (1H, m), 8.35-8.34 (1H, m), 7.97-7.93 (1H, m), 7.79 (1H, d), 3.96 (3H, s), 3.50-3.40 (1H, m), 3.09-2.99 (1H, m), 1.31 (3H, t)
Compound 6
 $^1$H-NMR (CDCl$_3$) δ: 8.78-8.77 (1H, m), 8.48-8.47 (1H, m), 8.31-8.29 (1H, m), 8.11-8.07 (1H, m), 7.76 (1H, d), 3.77 (3H, s), 3.47 (2H, q), 1.27 (3H, t)

In addition, the compounds produced according to the method described in the production examples described above are shown in Table 18 to Table 19.
Compounds Represented by Formula (2).

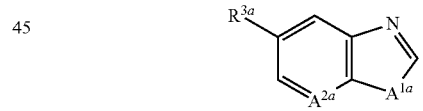

R$^{3a}$, A$^{1a}$ and A$^{2a}$ in the formula (2) represent the combinations shown in [Table 18] to [Table 19] shown below.

TABLE 18

| Intermediate Compound | R$^{3a}$ | A$^{1a}$ | A$^{2a}$ |
|---|---|---|---|
| 1 | CF$^3$ | S | N |
| 2 | CF$_2$CF$_3$ | NCH$_3$ | N |
| 3 | CF$_2$CF$_3$ | NCH$_3$ | CH |
| 4 | CF$_2$CF$_3$ | O | N |
| 5 | CF$_2$CF$_3$ | O | CH |
| 6 | CF$_2$CF$_3$ | S | N |
| 7 | CF$_2$CF$_3$ | S | CH |
| 8 | SCF$_3$ | NCH$_3$ | N |
| 9 | SCF$_3$ | NCH$_3$ | CH |
| 10 | SCF$_3$ | O | N |
| 11 | SCF$_3$ | O | CH |
| 12 | SCF$_3$ | S | N |

TABLE 18-continued

| Intermediate Compound | $R^{3a}$ | $A^{1a}$ | $A^{2a}$ |
|---|---|---|---|
| 13 | SOCF$_3$ | NCH$_3$ | N |
| 14 | SOCF$_3$ | NCH$_3$ | CH |
| 15 | SOCF$_3$ | O | N |
| 16 | SOCF$_3$ | O | CH |
| 17 | SOCF$_3$ | S | N |

TABLE 19

| Intermediate Compound | $R^{3a}$ | $A^1$ | $A^2$ |
|---|---|---|---|
| 18 | SO$_2$CF$_3$ | NCH3 | N |
| 19 | SO$_2$CF$_3$ | NCH3 | CH |
| 20 | SO$_2$CF$_3$ | O | N |
| 21 | SO$_2$CF$_3$ | O | CH |
| 22 | SO$_2$CF$_3$ | S | N |
| 23 | OCF$_3$ | NCH3 | N |
| 24 | OCF$_3$ | NCH3 | CH |
| 25 | OCF$_3$ | O | N |
| 26 | OCF$_3$ | O | CH |
| 27 | OCF$_3$ | S | N |
| 28 | CF(CF$_3$)$_2$ | NCH3 | N |
| 29 | CF(CF$_3$)$_2$ | NCH3 | CH |
| 30 | CF(CF$_3$)$_2$ | O | N |
| 31 | CF(CF$_3$)$_2$ | O | CH |
| 32 | CF(CF$_3$)$_2$ | S | N |
| 33 | CF(CF$_3$)$_2$ | S | CH |

$^1$H-NMR data of the compounds shown in [Table 18] to [Table 19] are shown below.
Intermediate Compound 5
$^1$H-NMR (CDCl$_3$) δ: 8.22 (1H, s), 8.09 (1H, s), 7.73 (1H, d), 7.66 (1H, d).
Next, formulation examples of the compound are shown. The part in the formulation example represents part by weight.

Formulation Example 1

10 parts of any one of Compounds 1 to 20 are dissolved in a mixture of 35 parts of xylene and 35 parts of N,N-dimethylformamide, and 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of anyone of Compounds 1 to 20 is further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds 1 to 20, and the mixture is mixed. Subsequently, an appropriate amount of water is added to this mixture, and the mixture is further stirred, granulated with a granulator, and forced-air dried to obtain each granule.

Formulation Example 4

1 part of any one of Compounds 1 to 20 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to obtain each dust formulation.

Formulation Example 5

35 parts of a mixture of polyoxyethylene alkyl ether sulfate ammonium salt and white carbon (weight ratio 1:1), 10 parts of any one of Compounds 1 to 20 and 55 parts of water are mixed, and finely pulverized by wet grinding method to obtain each flowable.

Formulation Example 6

0.1 parts of any one of Compounds 1 to 20 is dissolved in 5 parts of xylene and 5 parts of trichloroethane, and the mixture is mixed with 89.9 parts of deodorized kerosene to obtain each oil solution.

Formulation Example 7

10 mg of any one of Compounds 1 to 20 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

An aerosol can is filled with 0.1 parts of any one of Compounds 1 to 20 and 49.9 parts of Neothiozol (Chuo Kasei Co., Ltd.), and an aerosol valve is attached, and then the container is filled with 25 parts of dimethyl ether and 25 parts of LPG and shaken, and an actuator is attached to obtain an oil-based aerosol.

Formulation Example 9

0.6 parts of any one of Compounds 1 to 20, 0.01 parts of BHT (2,6-di-tert-butyl-4-methylphenol), 5 parts of xylene, 3.39 parts of deodorized kerosene and 1 part of emulsifier {Atmos 300 (registered trade name for Atmos Chemical Ltd.)} are mixed and dissolved, and an aerosol container is filled with the resulting solution and 50 parts of distilled water. Avalve is attached to the container, and then the container is filled with 40 parts of a propellant (LPG) under pressure through the valve to obtain an aqueous aerosol.

Formulation Example 10

0.1 g of any one of Compounds 1 to 20 is dissolved in 2 ml of propylene glycol, and the solution is impregnated in a porous ceramic plate with a size of 4.0×4.0 cm and 1.2 cm in thickness to obtain a heating type smoking agent.

Formulation Example 11

5 parts of any one of Compounds 1 to 20 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 12

5 parts of any one of Compounds 1 to 20 and 95 parts of a soft vinyl chloride resin are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 13

100 mg of any one of Compounds 1 to 20, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture was compressed to an appropriate size to obtain a tablet.

Formulation Example 14

25 mg of any one of Compounds 1 to 20, 60 mg of lactose, 25 mg of corn starch, 6 mg of carmellose calcium and an appropriate amount of 5% hydroxypropyl methylcellulose are mixed, and a hard shell gelatin capsule or a hydroxypropyl methylcellulose capsule is filled with the resulting mixture to obtain an encapsulated formulation.

Formulation Example 15

Distilled water is added to 1000 mg of anyone of Compounds 1 to 20, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final volume is 100 ml, and the mixture is mixed to obtain a suspension for oral administration.

Formulation Example 16

5 parts of any one of Compounds 1 to 20 are dissolved in 5 parts of polysorbate 85, 3 parts of benzyl alcohol, and 30 parts of propylene glycol, and a phosphate buffer is added to this solution so as to have a pH of 6.0 to 6.5, and then water is added until a total amount is 100 parts to obtain a liquid formulation for oral administration.

Formulation Example 17

5 parts of aluminum distearate are dispersed in 57 parts of fractionated palm oil and 3 parts of polysorbate 85 by heating. 25 parts of saccharin is dispersed in an oily vehicle obtained by cooling this dispersion to room temperature. 10 parts of any one of Compounds 1 to 20 is added thereto to obtain a paste formulation for oral administration.

Formulation Example 18

5 parts of any one of Compounds 1 to 20 and 95 parts of limestone filler are mixed, and a granule for oral administration is obtained using wet granulation method.

Formulation Example 19

5 parts of any one of Compounds 1 to 20 are dissolved in 80 parts of diethylene glycol monoethyl ether, and 15 parts of propylene carbonate is mixed therewith to obtain a spot-on solution.

Formulation Example 20

10 parts of any one of Compounds 1 to 20 are dissolved in 70 parts of diethylene glycol monoethyl ether, and 20 parts of 2-octyl dodecanol is mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds 1 to 20, and the mixture is sufficiently stirred and mixed until it becomes a uniform solution, and then 19.5 parts of water is added and further sufficiently stirred and mixed to obtain a shampoo agent as a uniform solution.

Formulation Example 22

0.15 parts of any one of Compounds 1 to 20, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds 1 to 20 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention is shown as test examples.

Test Example 1

The formulations of Compounds 1 to 3 and 9 to 10 as obtained in Formulation Example 5 were diluted with water, so as to have a concentration of the active ingredient of 500 ppm, to prepare a test drug solution.

On the other hand, on a cucumber seedling (the first true leaf stage) planted in a plastic cup was inoculated with about 30 *Aphis gossypii*, and leaving it for a day. 20 ml of the test drug solution was sprayed on the seedling.

Six days after spraying, the number of surviving *Aphis gossypii* parasitized on the leaves of the cucumber was examined, and the controlling value was calculated according to the following equation:

$$\text{Controlling value (\%)} = \{1-(Cb \times Tai)/(Cai \times Tb)\} \times 100$$

wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the test drug solution prepared by diluting the formulation not containing Compounds 1 to 3 or 9 to 10 as in Formulation Example 5 with the same amount of water as in the treated-section was sprayed.

As a result, in the treated-section using each test drug solution containing each of Compounds 1 to 3 and 9 to 10, the controlling value was 90% or more.

Test Example 2

The formulations of Compounds 2 to 3 as obtained in Formulation Example 5 were diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated about 30 *Aphis gossypii* (whole stage), and further kept in the greenhouse for 6 days, and then the number of surviving *Aphis gossypii* parasitized on the leaves of the cucumber was examined, and the controlling value was calculated according to the following equation:

Controlling value (%)={1−($Cb$×$Tai$)/($Cai$×$Tb$)}×100 wherein the symbols represent as follows:
Cb: the number of insects in a non-treated section before treatment,
Cai: the number of insects in a non-treated section on observation,
Tb: the number of insects in a treated section before treatment,
Tai: the number of insects in a treated section on observation,
wherein the non-treated section refers to a section where the test drug solution prepared by diluting the formulation not containing Compounds 2 to 3 as in Formulation Example 5 with the same amount of water as in the treated-section was sprayed.

As a result, in the treated-section using each test drug solution containing each of Compounds 2 to 3, the controlling value was 90% or more.

Test Example 3

The formulations of Compounds of Present Invention 9 to 10 as obtained in Formulation Example 5 were diluted with water, so as to have a concentration of the active ingredient of 500 ppm, to prepare a test drug solution.

On a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of *Nilaparvata lugens* parasitized on the rice was examined, and the controlling value was calculated according to the following equation:

Controlling value (%)={1−($Cb$×$Tai$)/($Cai$×$Tb$)}×100 wherein the symbols represent as follows:
Cb: the number of insects in a non-treated section before treatment,
Cai: the number of insects in a non-treated section on observation,
Tb: the number of insects in a treated section before treatment,
Tai: the number of insects in a treated section on observation,
wherein the non-treated section refers to a section where the test drug solution prepared by diluting the formulation not containing Compounds of Present Invention 9 to 10 as in Formulation Example 5 with the same amount of water as in the treated-section was sprayed.

As a result, in the treated-section of Compounds of Present Invention 9 to 10, the controlling value was 90% or more.

Test Example 4

The formulations of Compounds 1, 3 and 9 to 10 as obtained in Formulation Example 5 were diluted with water, so as to have a concentration of the active ingredient of 500 ppm, to prepare a test drug solution.

On the other hand, a rice seedling (2 weeks after sowing, the second leaf stage) planted in a plastic cup was drenched at its foot with 5 ml of each test drug solution, and kept in a greenhouse of 25° C. for 7 days. 20 third-fourth instar larvae of *Nilaparvata lugens* were released, and further kept in the greenhouse for 6 days, and then the number of surviving *Nilaparvata lugens* parasitized on the rice was examined, and the controlling value was calculated according to the following equation:

Controlling value (%)={1−($Cb$×$Tai$)/($Cai$×$Tb$)}×100 wherein the symbols represent as follows:
Cb: the number of insects in a non-treated section before treatment,
Cai: the number of insects in a non-treated section on observation,
Tb: the number of insects in a treated section before treatment,
Tai: the number of insects in a treated section on observation,
wherein the non-treated section refers to a section where the test drug solution prepared by diluting the formulation not containing Compounds 1, 3 or 9 to 10 as in Formulation Example 5 with the same amount of water as in the treated-section was sprayed.

As a result, in the treated-section using each test drug solution containing each of Compounds 1, 3 and 9 to 10, the controlling value was 90% or more.

Test Example 5

The formulations of Compounds 3 and 9 to 10 as obtained in Formulation Example 5 were diluted with water, so as to have a concentration of the active ingredient of 500 ppm, to prepare a test drug solution.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days, and when instar larvae hatched from the eggs, the above test drug solution was sprayed at a rate of 20 ml/cup, and the cup was kept in a greenhouse at 25° C. After 7 days, the number of surviving instar larvae on the tomato leaves was examined, and the controlling value was calculated according to the following equation:

Controlling value (%)={1−($Cb$×$Tai$)/($Cai$×$Tb$)}×100 wherein the symbols represent as follows:
Cb: the number of insects in a non-treated section before treatment,
Cai: the number of insects in a non-treated section on observation,
Tb: the number of insects in a treated section before treatment,
Tai: the number of insects in a treated section on observation,
wherein the non-treated section refers to a section where the test drug solution prepared by diluting the formulation not containing Compound 3 or 9 to 10 as in Formulation Example 5 with the same amount of water as in the treated-section was sprayed.

As a result, in the treated-section using each test drug solution containing each of Compounds 3 and 9 to 10, the controlling value was 90% or more.

Test Example 6

The formulations of Compounds 1 to 6 and 9 to 10 as obtained in Formulation Example 5 were diluted with water, so as to have a concentration of the active ingredient of 500 ppm, to prepare a test drug solution.

On the other hand, on cabbage at the third leaf stage planted in a polyethylene cup was sprayed at a rate 20 mL/cup of the test drug solution. After the drug solution was dried, the foliage part was cut off, and then placed in a 50 mL volume cup. Five second instar larvae of Plutella xylostella were released into the cup, and the cup was sealed with a lid. After the cup was kept at 25° C. for 5 days, the number of surviving insects was counted. The death rate was calculated according to the following equation:

Death rate (%)=(Number of dead insects/Number of tested insects)×100.

As a result, in the treated-section using each test drug solution containing each of Compounds 1 to 6 and 9 to 10, the death rate was 80% or more.

Test Example 7

The formulations of Compounds 1 to 6 and 9 to 10 as obtained in Formulation Example 5 were diluted with water, so as to have a concentration of the active ingredient of 500 ppm, to prepare a test spray solution.

On the other hand, an apple tree was planted in a plastic cup, and grown until the seventh-eighth true leaf was spread. To the apple tree was sprayed at a rate 20 mL/cup of the test drug solution. After the drug solution was dried, 60 first-instar Adoxophyes orana fasciata were released, and the plastic cup the bottom of which was cut off and on which a filter paper was put was upside-down and covered. After 7 days, the number of surviving insects was counted, and the death rate was calculated according to the following equation:

Death rate (%)=(Number of dead insects/Number of tested insects)×100.

As a result, in the treated-section of each test drug solution containing each of Compounds 1 to 6 and 9 to 10, the death rate was 90% or more.

Test Example 8

The formulations of Compounds 2 to 3 and 9 to 10 as obtained in Formulation Example 5 were diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 10 female imagoes of Musca domestica were released, and the cup was sealed with a lid. After 24 hours, the life and death of Musca domestica was examined, and the death rate was calculated.

As a result, in the treatment with Compounds 2 to 3 and 9 to 10, the death rate was 100% or more.

Test Example 9

The formulations of Compounds 3 and 10 as obtained in Formulation Example 5 were diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 2 male imagoes of Blattella germanica were released, and the cup was sealed with a lid. After 6 days, the life and death of Blattella germanica was examined, and the death rate was calculated.

As a result, in the treatment with Compounds 3 and 10, the death rate was 100%.

Test Example 10

The formulations of Compounds 1 to 3 and 9 to 10 as obtained in Formulation Example 5 were diluted with water, so as to have a concentration of the active ingredient of 500 ppm, to prepare a test drug solution.

0.7 ml of the test drug solution was added to 100 ml of ion-exchanged water (active ingredient concentration: 3.5 ppm). 20 last-instar larvae of Culex pipiens pallens were released into the solution. One day later, the life and death of the Culex pipiens pallens was examined, and the death rate of the pest was calculated.

As a result, in the treatment with Compounds 1 to 3 and 9 to 10, the death rate was 91% or more.

Test Example 11

2 mg of the compound of the present invention is weighed in a screw tube (Maruemu No. 5; 27×55 mm), and 0.2 mL of acetone is added thereto and sealed with a cap to dissolve the compound. The screw tube is rotated and inverted to uniformity coat the drug solution onto the whole inner wall of the tube. After removing the cap, the solution is air-dried for about 2 hours, and then non-blood-sucking nymphal ticks, Haemaphysalis longicornis (5 ticks/group) are released, and the tube is sealed with the cap. After 2 days, the number of dead ticks is examined, and the death rate is calculated according to the following equation:

Death rate (%)=100×(Number of dead ticks/Number of tested ticks).

As a result, the sufficient death rate is obtained by the treatment with the compound of the present invention.

INDUSTRIAL APPLICABILITY

The compound of the present invention has a controlling effect on pests and is useful as an active ingredient of a pest control agent.

The invention claimed is:

1. A fused heterocyclic compound represented by formula (1):

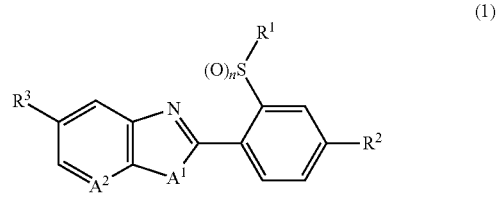

wherein
A$^1$ represents —NR$^4$—, a sulfur atom or an oxygen atom,
A$^2$ represents a nitrogen atom or =CH—,
R$^1$ represents an ethyl group, a cyclopropyl group or a cyclopropylmethyl group,
R$^2$ represents —S(O)$_m$R$^6$ or —C(R$^7$)(CF$_3$)$_2$, R³ represents a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, R⁴ represents a C1 to C6 alkyl group optionally having one or more halogen atoms, R⁶ represents a C1 to C6 haloalkyl group, R⁷ represents a fluorine atom or a chlorine atom, m represents 0, 1, or 2, and n represents 0, 1, or 2, wherein when R³ represents a trifluoromethyl group, A¹ represents a sulfur atom and A² represents a nitrogen atom, and when A¹ represents a sulfur atom and A² represents =CH—, R³ represents a C2 to C3 perfluoroalkyl group, a C2 to C3 perfluoroalkoxy group, a C2 to C3 perfluoroalkylsulfanyl group, a C2 to C3 perfluoroalkylsulfinyl group or a C2 to C3 perfluoroalkylsulfonyl group.

2. The compound according to claim 1, wherein A¹ is —NR⁴—.

3. The compound according to claim 1, wherein A¹ is a sulfur atom.

4. The compound according to claim 1, wherein A¹ is an oxygen atom.

5. The compound according to claim 1, wherein A² is =CH—.

6. The compound according to claim 1, wherein A² is a nitrogen atom.

7. A pest control composition comprising the compound as defined in claim 1, and an inert carrier.

8. A method for controlling pests comprising applying an effective amount of the compound as defined in claim 1 to a pest or a pest-infested area.

9. A method for producing a compound represented by formula (1):

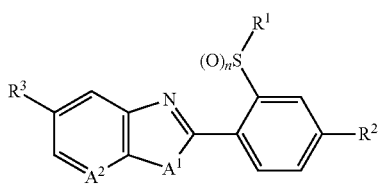

wherein A¹, A², R¹, R², R³, R⁴, R⁶, R⁷, m and n represent the same meaning as described below, by reacting an intermediate compound (M7):

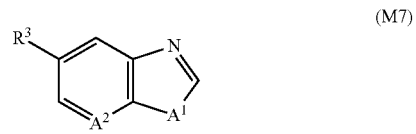

wherein

A¹ is —NR⁴—, a sulfur atom or an oxygen atom,

A² represents a nitrogen atom or =CH—,

R³ represents a C1 to C3 perfluoroalkyl group, a C1 to C3 perfluoroalkoxy group, a C1 to C3 perfluoroalkylsulfanyl group, a C1 to C3 perfluoroalkylsulfinyl group or a C1 to C3 perfluoroalkylsulfonyl group, R⁴ represents a C1 to C6 alkyl group optionally having one or more halogen atoms, and n represents 0, 1, or 2, with an intermediate compound (M8):

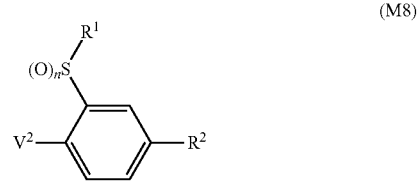

wherein

R¹ represents an ethyl group, a cyclopropyl group or a cyclopropylmethyl group,

R² represents —S(O)$_m$R⁶ or —C(R⁷)(CF₃)₂,

R⁶ represents a C1 to C6 haloalkyl group,

R⁷ represents a fluorine atom or a chlorine atom,

V² represents a bromine atom or an iodine atom, and n represents 0, 1, or 2, in the presence of a palladium catalyst, a copper catalyst, a ligand and a base.

* * * * *